US012653685B2

(12) United States Patent
Incavo

(10) Patent No.: US 12,653,685 B2
(45) Date of Patent: Jun. 16, 2026

(54) KNEE ARTHROPLASTY WITH MODULAR FEMORAL ADAPTERS

(71) Applicant: Stephen J. Incavo, Houston, TX (US)

(72) Inventor: Stephen J. Incavo, Houston, TX (US)

( * ) Notice: Subject to any disclaimer, the term of this patent is extended or adjusted under 35 U.S.C. 154(b) by 0 days.

(21) Appl. No.: 18/418,255

(22) Filed: Jan. 20, 2024

(65) Prior Publication Data

US 2024/0156607 A1     May 16, 2024

Related U.S. Application Data

(63) Continuation of application No. 17/168,362, filed on Feb. 5, 2021, now Pat. No. 11,890,198, which is a continuation of application No. 16/143,154, filed on Sep. 26, 2018, now Pat. No. 10,925,743.

(60) Provisional application No. 62/563,108, filed on Sep. 26, 2017.

(51) Int. Cl.
*A61F 2/38*          (2006.01)
*A61F 2/30*          (2006.01)
(52) U.S. Cl.
CPC ............ *A61F 2/384* (2013.01); *A61F 2/3859* (2013.01); *A61F 2/3886* (2013.01); *A61F 2/389* (2013.01); *A61F 2002/30153* (2013.01); *A61F 2002/30471* (2013.01); *A61F 2002/30528* (2013.01); *A61F 2002/30604* (2013.01); *A61F 2002/30624* (2013.01); *A61F 2002/3069* (2013.01)
(58) Field of Classification Search
CPC ...... A61F 2/384; A61F 2/3859; A61F 2/3886; A61F 2/389; A61F 2002/30616
See application file for complete search history.

(56) References Cited

U.S. PATENT DOCUMENTS

| | | | | |
|---|---|---|---|---|
| 4,216,549 A | * | 8/1980 | Hillberry .............. | A61F 2/3868 623/20.26 |
| 4,224,697 A | * | 9/1980 | Murray ................. | A61F 2/3836 623/20.25 |
| 5,100,409 A | * | 3/1992 | Coates ............... | A61B 17/1764 606/88 |
| 5,176,684 A | * | 1/1993 | Ferrante ................. | A61F 2/461 606/86 R |
| 5,358,527 A | * | 10/1994 | Forte .................... | A61F 2/3845 623/20.27 |

(Continued)

FOREIGN PATENT DOCUMENTS

| | | | | |
|---|---|---|---|---|
| DE | 4102509 A | * | 7/1992 | .............. A61F 2/38 |
| EP | 3260086 A1 | * | 12/2017 | .......... A61F 2/3886 |
| WO | WO-2012016002 A1 | * | 2/2012 | .............. A61F 2/38 |

*Primary Examiner* — Alvin J Stewart
(74) *Attorney, Agent, or Firm* — David Meibos; Maywood IP Law

(57)          ABSTRACT

An arthroplasty system may include a first prosthesis to be fixed to a first bone of a joint, a second prosthesis to be fixed to a second bone of the joint for articulation with the first prosthesis, and one or more adapters to be fixed to the first prosthesis for articulation with the second prosthesis to modify the stability of the second prosthesis relative to the first prosthesis. The system may include one or more articular inserts to be coupled to the second prosthesis for articulation with the first prosthesis and/or the adapter(s). The articular inserts may be fixed or mobile bearing relative to the second prosthesis. Each adapter and corresponding articular insert may modify stability differently.

18 Claims, 28 Drawing Sheets

(56) References Cited

U.S. PATENT DOCUMENTS

| | | | | |
|---|---|---|---|---|
| 5,370,701 A * | 12/1994 | Finn | A61F 2/385 | 623/20.25 |
| 5,411,555 A * | 5/1995 | Nieder | A61F 2/384 | 623/20.26 |
| 5,549,687 A * | 8/1996 | Coates | A61F 2/3886 | 606/88 |
| 5,776,201 A * | 7/1998 | Colleran | A61F 2/4684 | 606/88 |
| 5,824,102 A * | 10/1998 | Buscayret | A61F 2/385 | 623/20.21 |
| 5,954,770 A * | 9/1999 | Schmotzer | A61F 2/385 | 623/20.24 |
| 6,080,195 A * | 6/2000 | Colleran | A61F 2/3886 | 623/20.32 |
| 6,117,175 A * | 9/2000 | Bosredon | A61F 2/3854 | 623/20.15 |
| 6,143,034 A | 11/2000 | Burrows | A61F 2/384 | 623/20.29 |
| 6,447,549 B1 * | 9/2002 | Taft | A61F 2/38 | 623/20.14 |
| 6,485,519 B2 * | 11/2002 | Meyers | A61F 2/3868 | 623/20.14 |
| 6,629,999 B1 * | 10/2003 | Serafin, Jr. | A61F 2/3886 | 623/20.15 |
| 6,719,800 B2 * | 4/2004 | Meyers | A61F 2/385 | 623/18.11 |
| 6,972,039 B2 * | 12/2005 | Metzger | A61F 2/3868 | 623/20.29 |
| 7,303,586 B2 * | 12/2007 | Keller | A61F 2/384 | 623/20.29 |
| 7,507,256 B2 * | 3/2009 | Heck | A61F 2/384 | 623/20.15 |
| 7,658,767 B2 * | 2/2010 | Wyss | A61F 2/385 | 623/20.29 |
| 7,780,736 B2 * | 8/2010 | Wasielewski | A61F 2/3886 | 623/20.14 |
| 7,842,093 B2 * | 11/2010 | Peters | A61F 2/3886 | 623/20.15 |
| 7,918,893 B2 * | 4/2011 | Romeis | A61F 2/385 | 623/20.24 |
| 8,268,006 B2 * | 9/2012 | Meyers | A61F 2/385 | 623/20.29 |
| 8,545,571 B2 * | 10/2013 | Collazo | A61F 2/38 | 623/20.27 |
| 8,628,579 B2 * | 1/2014 | Ries | A61F 2/3886 | 623/20.29 |
| 8,932,365 B2 * | 1/2015 | Parisi | A61F 2/3868 | 623/20.27 |
| 9,119,734 B2 * | 9/2015 | Dees | A61F 2/3859 | |
| 9,358,116 B2 * | 6/2016 | Bartel | A61F 2/3804 | |
| 9,585,758 B2 * | 3/2017 | Metzger | A61F 2/3836 | |
| 10,064,732 B2 * | 9/2018 | Lu | A61F 2/389 | |
| 10,064,733 B2 * | 9/2018 | Metzger | A61F 2/389 | |
| 10,363,147 B2 * | 7/2019 | Tsukayama | A61F 2/389 | |
| 10,682,236 B2 * | 6/2020 | Boettiger | A61F 2/384 | |
| 10,736,748 B2 * | 8/2020 | Reeder | A61F 2/3868 | |
| 10,925,743 B2 * | 2/2021 | Incavo | A61F 2/3886 | |
| 11,547,570 B2 * | 1/2023 | Parisi | A61F 2/30749 | |
| 11,890,198 B2 * | 2/2024 | Incavo | A61F 2/384 | |
| 2002/0103541 A1 * | 8/2002 | Meyers | A61F 2/3868 | 623/20.24 |
| 2003/0009228 A1 * | 1/2003 | Meyers | A61F 2/3868 | 623/20.24 |
| 2003/0009229 A1 * | 1/2003 | Pappas | A61F 2/3886 | 623/20.29 |
| 2003/0009231 A1 * | 1/2003 | Gundlapalli | A61F 2/30942 | 623/20.29 |
| 2003/0158606 A1 * | 8/2003 | Coon | A61F 2/38 | 623/20.15 |
| 2004/0039450 A1 * | 2/2004 | Griner | A61B 17/155 | 606/88 |
| 2004/0083003 A1 * | 4/2004 | Wasielewski | A61L 27/3604 | 623/20.21 |
| 2004/0162620 A1 * | 8/2004 | Wyss | A61F 2/3886 | 623/20.29 |
| 2005/0107886 A1 * | 5/2005 | Crabtree | A61F 2/385 | 623/20.29 |
| 2005/0246028 A1 * | 11/2005 | Pappas | A61F 2/385 | 623/20.29 |
| 2006/0167555 A1 * | 7/2006 | Heck | A61F 2/3672 | 623/20.35 |
| 2006/0167560 A1 * | 7/2006 | Heck | A61F 2/384 | 623/20.15 |
| 2006/0173463 A1 * | 8/2006 | Dees | A61F 2/4684 | 606/88 |
| 2008/0004708 A1 * | 1/2008 | Wyss | A61F 2/385 | 623/20.28 |
| 2008/0167722 A1 * | 7/2008 | Metzger | A61F 2/30721 | 623/20.29 |
| 2009/0005875 A1 * | 1/2009 | Koenemann | A61F 2/3859 | 623/20.35 |
| 2009/0088860 A1 * | 4/2009 | Romeis | A61F 2/385 | 623/20.27 |
| 2009/0125114 A1 * | 5/2009 | May | A61F 2/38 | 623/20.14 |
| 2009/0143866 A1 * | 6/2009 | Servidio | A61F 2/385 | 623/20.14 |
| 2009/0299482 A1 * | 12/2009 | Metzger | A61F 2/38 | 623/20.29 |
| 2009/0319048 A1 * | 12/2009 | Shah | A61F 2/3886 | 623/20.29 |
| 2010/0174378 A1 * | 7/2010 | Metzger | A61F 2/30721 | 623/20.28 |
| 2010/0211179 A1 * | 8/2010 | Angibaud | A61F 2/3886 | 623/20.27 |
| 2010/0222891 A1 * | 9/2010 | Goodfried | A61F 2/3859 | 623/20.36 |
| 2010/0286788 A1 * | 11/2010 | Komistek | A61F 2/3877 | 623/20.23 |
| 2012/0029649 A1 * | 2/2012 | Collazo | A61F 2/3859 | 623/20.28 |
| 2012/0323335 A1 * | 12/2012 | Parisi | A61F 2/3859 | 623/20.35 |
| 2014/0277535 A1 * | 9/2014 | Metzger | A61F 2/3886 | 623/20.29 |
| 2017/0027706 A1 * | 2/2017 | Hagen | A61F 2/3845 | |
| 2017/0128219 A1 * | 5/2017 | Metzger | A61F 2/3868 | |
| 2017/0312087 A1 * | 11/2017 | Faccioli | A61F 2/385 | |
| 2017/0333207 A1 * | 11/2017 | Tsukayama | A61B 17/1675 | |
| 2018/0125667 A1 * | 5/2018 | Savage | A61F 2/389 | |
| 2018/0243100 A1 * | 8/2018 | Boettiger | A61F 2/384 | |
| 2019/0029830 A1 * | 1/2019 | Nguyen | A61F 2/30734 | |
| 2019/0091030 A1 * | 3/2019 | Incavo | A61F 2/384 | |
| 2019/0350723 A1 * | 11/2019 | Lashure | A61F 2/461 | |
| 2020/0046506 A1 * | 2/2020 | Jang | A61F 2/385 | |
| 2020/0046508 A1 * | 2/2020 | Parisi | A61F 2/30749 | |
| 2020/0069432 A1 * | 3/2020 | McMinn | A61F 2/3859 | |
| 2020/0246150 A1 * | 8/2020 | Matyas | A61F 2/3859 | |
| 2021/0307914 A1 * | 10/2021 | Matyas | A61F 2/384 | |
| 2022/0096244 A1 * | 3/2022 | Reeder | A61F 2/4684 | |
| 2023/0024863 A1 * | 1/2023 | Bowman | A61F 2/3859 | |

* cited by examiner

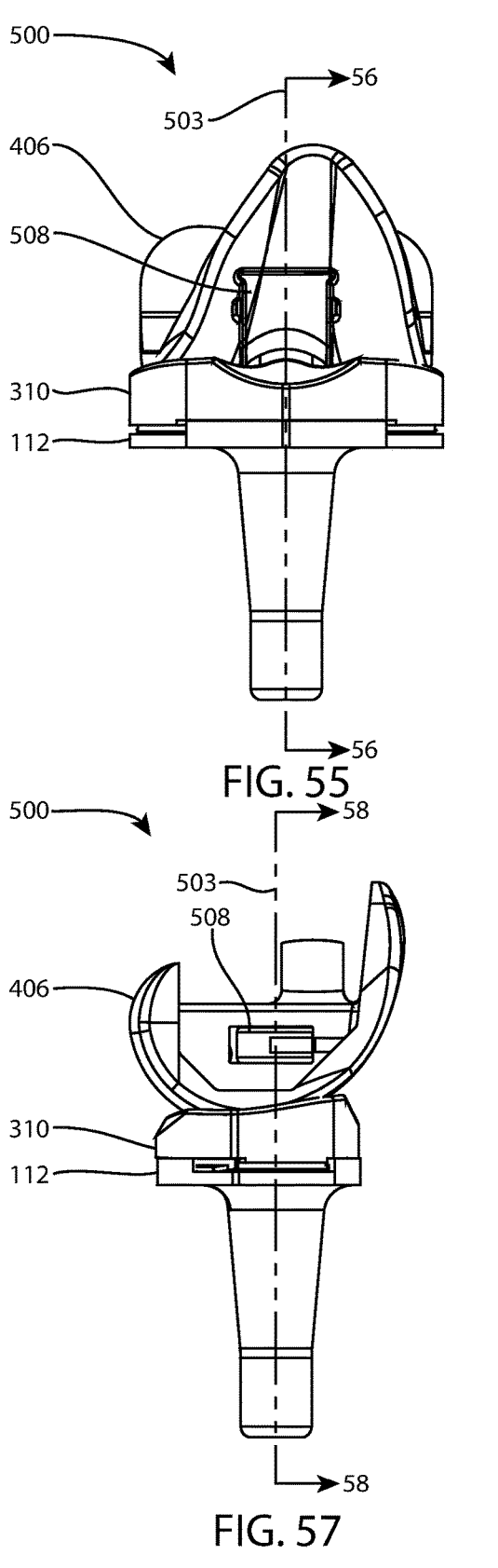
FIG. 55
FIG. 57
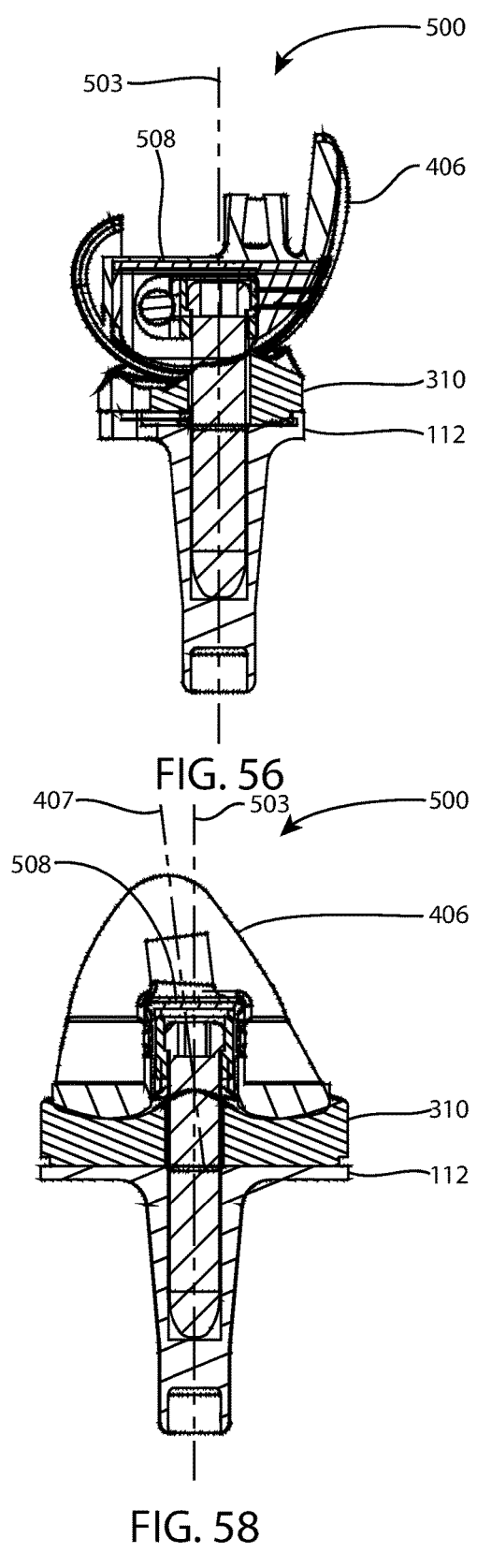
FIG. 56
FIG. 58

KNEE ARTHROPLASTY WITH MODULAR FEMORAL ADAPTERS

CROSS-REFERENCE TO RELATED APPLICATIONS

The present application is a continuation of U.S. patent application Ser. No. 17/168,362 filed on Feb. 5, 2021, entitled KNEE ARTHROPLASTY WITH MODULAR FEMORAL ADAPTERS, which is a continuation of U.S. patent application Ser. No. 16/143,154 filed on Sep. 26, 2018 entitled KNEE ARTHROPLASTY WITH MODULAR FEMORAL ADAPTERS that issued on Feb. 23, 2021 as U.S. Pat. No. 10,925,743, which claims the benefit of U.S. Provisional Patent Application No. 62/563,108, filed on Sep. 26, 2017, entitled IMPLANTABLE ORTHOPEDIC KNEE JOINT PROSTHESES, KITS, AND METHODS WITH REMOVABLE FEMORAL ADAPTORS. The foregoing are incorporated by reference as though set forth herein in their entirety.

TECHNICAL FIELD

The present disclosure relates to implantable medical devices. More specifically, the present disclosure relates to arthroplasty systems with modular adapters to provide various degrees of constraint or stability between articulating prostheses. While the current disclosure is made in the context of knee arthroplasty, the principles described herein are applicable to arthroplasty systems for other joints around the body.

BACKGROUND

Arthroplasty prostheses are designed to articulate together to provide motion at a joint. The prostheses may be designed with more or less constraint in the articulation, according to the design rationale and intended use. For example, in knee arthroplasty, less constrained prostheses may be designed for use in patients with robust soft tissue structures around the knee, for example in primary (first) surgeries. Less constrained prostheses tend to provide greater range of motion. More highly constrained prostheses may be designed for use in patients whose soft tissues and/or other anatomical structures of the knee are compromised, as is often the case in revision (second and subsequent) surgeries. More constrained prostheses tend to provide greater stability to the articulation.

Two types of constrained knee prostheses are the constrained condylar knee (CCK) and the hinged knee. A CCK design may be used to counteract anterior-posterior laxity or instability and/or lateral collateral ligament (LCL) laxity in patients with an intact medial collateral ligament (MCL) where the surgeon achieves stability when the knee is flexed to 90 degrees (a stable "flexion space"). A CCK design provides stability in the anterior-posterior direction and/or mild medial-lateral stability. A hinge design may be used in patients with a deficient MCL or a flexion space that is too large (unstable). A hinge design provides stability in the anterior-posterior and medial-lateral directions, and can stabilize an unstable flexion space. Conventionally, a surgeon decides upon a constrained prosthesis during preoperative planning.

There is a need for arthroplasty technology that enables a surgeon to choose a constraint level during the arthroplasty procedure, for example, choosing a CCK or hinged knee during a knee arthroplasty procedure. There is also a need for arthroplasty technology that enables a surgeon to convert a prosthesis from one constraint level to another in a subsequent procedure, for example, converting a previously-implanted CCK knee to a hinged knee, or vice versa, in a subsequent relatively minor surgery.

SUMMARY

The various systems and methods of the present technology have been developed in response to the present state of the art, and in particular, in response to the problems and needs in the art that have not yet been fully solved by currently available arthroplasty systems. The systems and methods of the present technology may provide adapters and articular inserts that may be selected intraoperatively during an initial surgery, or during a later revision surgery, to modify the stability of an arthroplasty system.

To achieve the foregoing, and in accordance with the technology as embodied and broadly described herein, in an aspect of the technology, an arthroplasty system for a joint between a first bone and a second bone, the system including: a first arthroplasty prosthesis with a receptacle, wherein the first arthroplasty prosthesis is configured to be fixed to the first bone and to articulate against a second arthroplasty prosthesis which is configured to be fixed to the second bone, so as to provide a range of motion between the first and second arthroplasty prostheses; and an adapter removably fixed in the receptacle, wherein the adapter includes a first constraint feature for constrained articulation against a complementary second constraint feature of the second arthroplasty prosthesis to modify the range of motion.

Embodiments of this aspect may include any of the following attributes. The adapter is insertable into, fixable within, and removable from the receptacle when the first arthroplasty prosthesis is fixed to the first bone. The adapter goes into the receptacle along a direction that is generally parallel to a mechanical axis of the first bone when the first arthroplasty prosthesis is fixed to the first bone. The receptacle includes an alcove extending into the first arthroplasty prosthesis along the direction, a first insertion stop feature, and a first removal stop feature, wherein the alcove includes a non-circular cross-sectional shape perpendicular to the direction; wherein the adapter includes a non-circular exterior cross-sectional shape perpendicular to the direction, a second insertion stop feature, and a second removal stop feature, wherein the adapter exterior cross-sectional shape is complementary to the alcove cross-sectional shape; wherein when the adapter is in the receptacle, the adapter exterior cross-sectional shape fits closely within the alcove cross-sectional shape, the first and second insertion stop features are engaged to prevent over-insertion of the adapter into the receptacle, and the first and second removal stop features are engaged to prevent unintentional removal of the adapter out of the receptacle, wherein the first and second removal stop features are disengageable. The adapter goes into the receptacle along a direction that is generally perpendicular to a mechanical axis of the first bone when the first arthroplasty prosthesis is fixed to the first bone. The receptacle includes an alcove extending into the first arthroplasty prosthesis along the direction, a first insertion stop feature, and a first removal stop feature, wherein the alcove includes a non-circular cross-sectional shape perpendicular to the direction; wherein the adapter includes a non-circular exterior cross-sectional shape perpendicular to the direction, a second insertion stop feature, and a second removal stop feature, wherein the adapter exterior cross-sectional shape is complementary to the alcove cross-sectional shape; wherein when the adapter is in the receptacle, the adapter exterior cross-sectional shape fits closely within the alcove cross-sectional shape, the first and second insertion stop features are engaged to prevent over-insertion of the adapter into the receptacle, and the first and second removal stop features are engaged to prevent unintentional removal of the adapter out of the receptacle, wherein the first and second removal stop features are disengageable. The first constraint feature includes a cavity; wherein the second constraint feature includes a protrusion received in the cavity so that when the joint is extended, the second arthroplasty prosthesis has limited translation along a direction that is generally perpendicular to a mechanical axis of the first bone, and so that when the joint is flexed, the second arthroplasty prosthesis has limited translation along a direction that is generally parallel to the mechanical axis of the first bone. The first constraint feature includes a main body coupled to a sleeve by a hinge so that the sleeve rotates relative to the main body about a hinge axis, wherein the sleeve includes a bore; wherein the first constraint feature further includes a shaft that is fixed in the bore; wherein the second constraint feature includes a hole that receives the shaft, so that the shaft rotates within the hole about a central longitudinal shaft axis and translates within the hole along the shaft axis.

In another aspect of the technology, an arthroplasty system for a joint between a first bone and a second bone, the system including: a first arthroplasty prosthesis configured to be fixed to the first bone, wherein the first arthroplasty prosthesis includes a receptacle; an adapter removably fixed in the receptacle, wherein the adapter includes a first constraint feature; and a second arthroplasty prosthesis configured to be fixed to the second bone, wherein the first and second arthroplasty prostheses articulate together to provide a range of motion between the first and second arthroplasty prostheses, wherein the second arthroplasty prosthesis includes a second constraint feature that articulates against the first constraint feature to increase stability of the first arthroplasty prosthesis relative to the second arthroplasty prosthesis.

Embodiments of this aspect may include any of the following attributes. The adapter is insertable into, fixable within, and removable from the receptacle when the first arthroplasty prosthesis is fixed to the first bone. The adapter goes into the receptacle along a direction that is generally parallel to a mechanical axis of the first bone when the first arthroplasty prosthesis is fixed to the first bone. The receptacle includes an alcove extending into the first arthroplasty prosthesis along the direction, a first insertion stop feature, and a first removal stop feature, wherein the alcove includes a non-circular cross-sectional shape perpendicular to the direction; wherein the adapter includes a non-circular exterior cross-sectional shape perpendicular to the direction, a second insertion stop feature, and a second removal stop feature, wherein the adapter exterior cross-sectional shape is complementary to the alcove cross-sectional shape; wherein when the adapter is in the receptacle, the adapter exterior cross-sectional shape fits closely within the alcove cross-sectional shape, the first and second insertion stop features are engaged to prevent over-insertion of the adapter into the receptacle, and the first and second removal stop features are disengageable. The adapter goes into the receptacle along a direction that is generally perpendicular to a mechanical axis of the first bone when the first arthroplasty prosthesis is fixed to the first bone. The receptacle includes an alcove extending into the first arthroplasty prosthesis along the direction, a first insertion stop feature, and a first removal stop feature, wherein the alcove includes a non-circular cross-sectional shape perpendicular to the direction; wherein the adapter includes a non-circular exterior cross-sectional shape perpendicular to the direction, a second insertion stop feature, and a second removal stop feature, wherein the adapter exterior cross-sectional shape is complementary to the alcove cross-sectional shape; wherein when the adapter is in the receptacle, the adapter exterior cross-sectional shape fits closely within the alcove cross-sectional shape, the first and second insertion stop features are engaged to prevent over-insertion of the adapter into the receptacle, and the first and second removal stop features are engaged to prevent unintentional removal of the adapter out of the receptacle, wherein the first and second removal stop features are disengageable. The first constraint feature includes a cavity; wherein the second constraint feature includes a protrusion received in the cavity so that when the joint is extended, the second arthroplasty prosthesis has limited translation along a direction that is generally perpendicular to a mechanical axis of the first bone, and so that when the joint is flexed, the second arthroplasty prosthesis has limited translation along a direction that is generally parallel to the mechanical axis of the first bone. The first constraint feature includes a main body coupled to a sleeve by a hinge so that the sleeve rotates relative to the main body about a hinge axis, wherein the sleeve includes a bore; wherein the first constraint feature further includes a shaft that is fixed in the bore; wherein the second constraint feature includes a hole that receives the shaft, so that the shaft rotates within the hole about a central longitudinal shaft axis and translates within the hole along the shaft axis.

In another aspect of the technology, an arthroplasty system for a joint between a first bone and a second bone, the system including: an adapter including a first constraint feature, wherein the adapter is removably fixable to a first arthroplasty prosthesis, wherein the first arthroplasty prosthesis is configured to be fixed to the first bone; and a second arthroplasty prosthesis including a second constraint feature, wherein the second arthroplasty prosthesis is configured to be fixed to the second bone and to articulate against the first arthroplasty prosthesis; wherein the second constraint feature articulates against the first constraint feature to increase stability of the first arthroplasty prosthesis relative to the second arthroplasty prosthesis.

Embodiments of this aspect may include any of the following attributes. The adapter is fixable to, and removable from, the first arthroplasty prosthesis when the first arthroplasty prosthesis is fixed to the first bone. The adapter is fixable to, and removable from, the first arthroplasty prosthesis along a direction that is generally parallel to a mechanical axis of the first bone when the first arthroplasty prosthesis is fixed to the first bone. The adapter is fixable to, and removable from, the first arthroplasty prosthesis along a direction that is generally perpendicular to a mechanical axis of the first bone when the first arthroplasty prosthesis is fixed to the first bone. The first constraint feature includes a cavity; wherein the second constraint feature includes a protrusion received in the cavity so that when the joint is extended, the second arthroplasty prosthesis has limited translation along a direction that is generally perpendicular to a mechanical axis of the first bone, and so that when the joint is flexed, the second arthroplasty prosthesis has limited translation along a direction that is generally parallel to the mechanical axis of the first bone. The first constraint feature includes a main body coupled to a sleeve by a hinge so that the sleeve rotates relative to the main body about a hinge axis, wherein the sleeve includes a bore; wherein the first constraint feature further includes a shaft that is fixed in the bore; wherein the second constraint feature includes a hole that receives the shaft, so that the shaft rotates within the hole about a central longitudinal shaft axis and translates within the hole along the shaft axis.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 55 is an anterior view of the knee arthroplasty system of FIG. 51, in extension;

FIG. 56 is a cross-sectional view of the knee arthroplasty system of FIG. 55, taken along section line 56-56 of FIG. 55;

FIG. 57 is a medial view of the knee arthroplasty system of FIG. 51, in extension;

FIG. 58 is a cross-sectional view of the knee arthroplasty system of FIG. 57, taken along section line 58-58 of FIG. 57;

DETAILED DESCRIPTION

Figure 1:
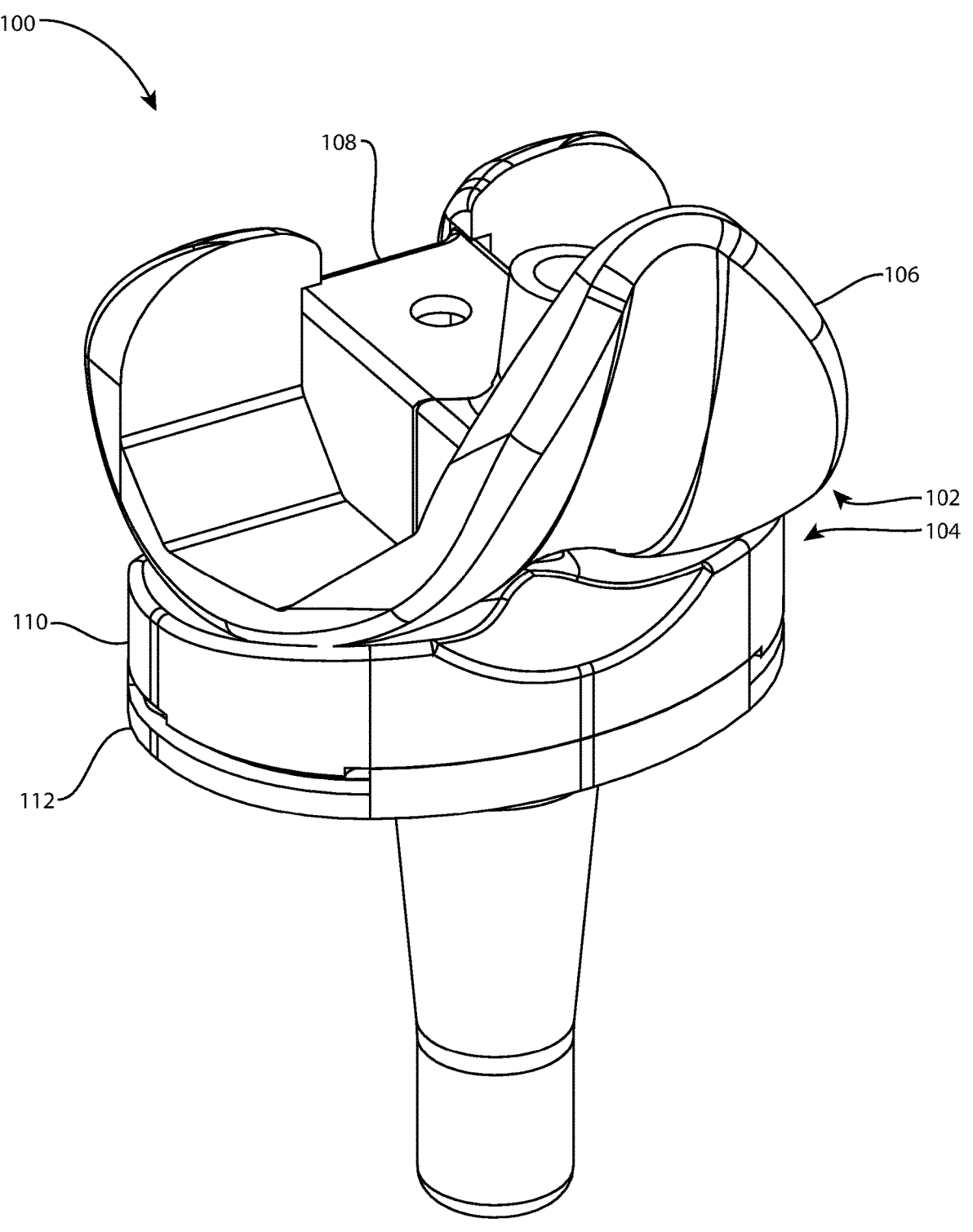
FIG. 1 is an oblique view of a knee arthroplasty system, in extension.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with," and equivalents, refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The phrase "fixed to," and equivalents, refers to two or more entities that are coupled together so as to substantially eliminate relative motion between the entities. Two entities may be functionally fixed to each other even though they are not in direct contact with each other.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. While these terms are commonly used to refer to the human body, certain terms are applicable to physical objects in general. In this specification, standard knee anatomical terms are employed with their ordinary and customary meanings.

A standard system of three mutually perpendicular reference planes is employed. A sagittal plane, or lateral plane, divides a body into right and left portions. A coronal plane, or frontal plane, divides a body into anterior and posterior portions. A transverse plane, or axial plane, divides a body into superior and inferior portions. The sagittal, coronal, and transverse planes are mutually perpendicular. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. Varus means deviation of the distal part of the leg below the knee inward, resulting in a bowlegged appearance. Valgus means deviation of the distal part of the leg below the knee outward, resulting in a knock-kneed appearance.

An anatomical axis of a long bone extends along the bone and is centered in the diaphysis, or shaft. A mechanical axis of a long bone extends along the bone between the centers of its epiphyses (articular ends). For example, the mechanical axis of the femur extends between the center of the femoral head at the proximal end and the center of the intercondylar notch at the distal end.

An arthroplasty system may include one or more arthroplasty prostheses, each of which may be a unitary component or an assembly of multiple component. For example, a knee arthroplasty system may include a femoral prosthesis, a tibial prosthesis, and/or a patellar prosthesis, each of which may be a unitary component or an assembly of multiple components. An arthroplasty system may also include surgical instruments for preparing the bone, determining implant sizes, and inserting or removing prostheses.

In this specification, "substantially" means±15% for linear measurements and ±22.5° for angular measurements. "Generally" means±30% for linear measurements and ±45° for angular measurements.

Referring to FIGS. 1-18, a knee arthroplasty system 100 may include a femoral prosthesis 102 and/or a tibial prosthesis 104. This embodiment may be referred to as a distal CCK fixed design. A left knee design is shown. The femoral prosthesis 102 may include a femoral component 106 and an adapter 108. The femoral prosthesis 102 may include additional components, such as a femoral intramedullary stem (not shown) or defect-filling augments (not shown). Referring to FIGS. 11-14, axis 103 corresponds to the femoral mechanical axis. The tibial prosthesis 104 may include a tibial articular insert 110 and a tibial baseplate 112, or the tibial articular insert and tibial baseplate may be integrally formed as a single component. The tibial prosthesis 104 may include additional components, such as an intramedullary stem (not shown) or defect-filling augments (not shown).

Figures 11, 12, 13, 14:
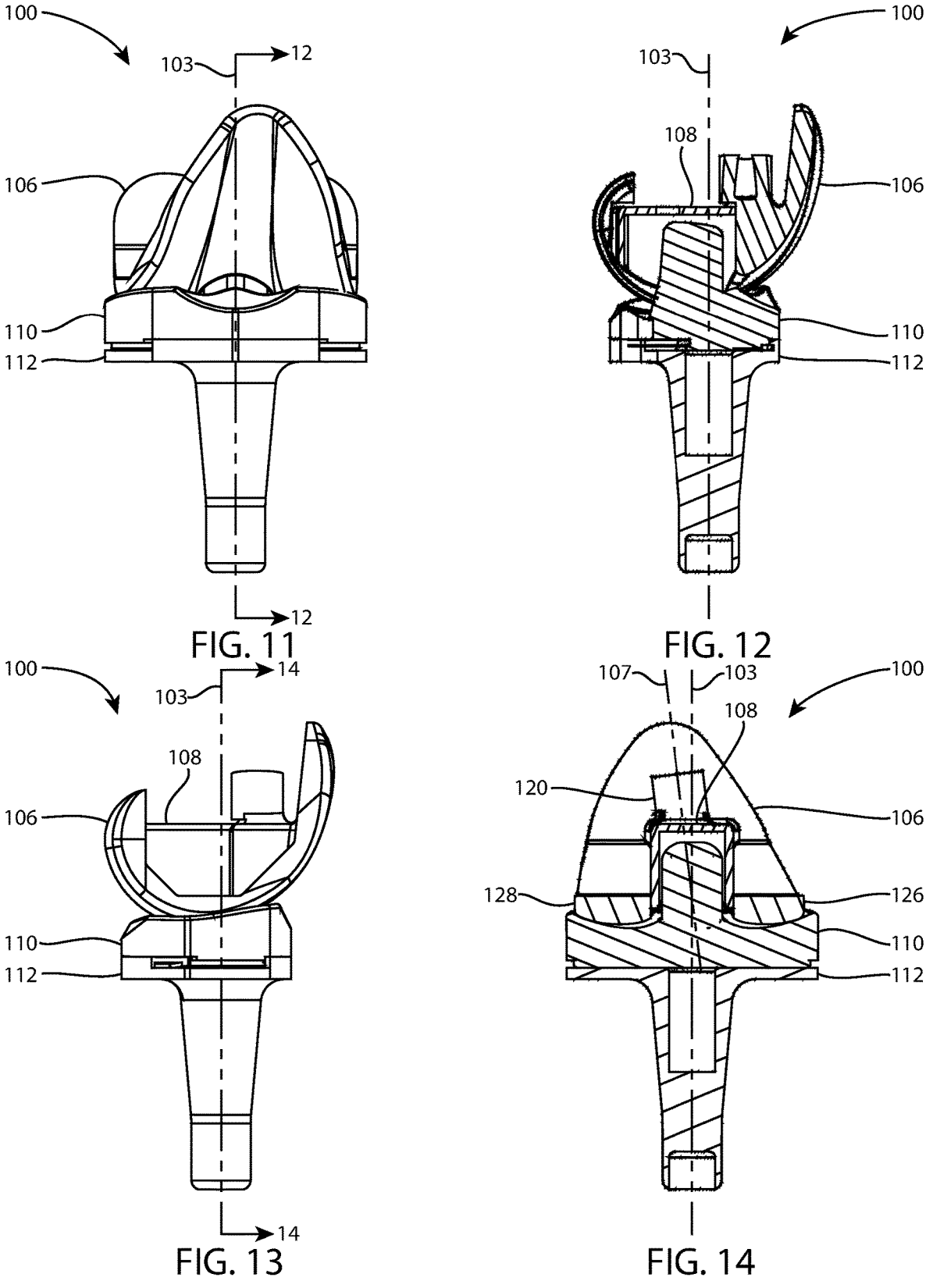
FIG. 11 is an anterior view of the knee arthroplasty system of FIG. 1, in extension.
FIG. 12 is a cross-sectional view of the knee arthroplasty system of FIG. 11, taken along section line 12-12 of FIG. 11.
FIG. 13 is a medial view of the knee arthroplasty system of FIG. 1, in extension.
FIG. 14 is a cross-sectional view of the knee arthroplasty system of FIG. 13, taken along section line 14-14 of FIG. 13.

The femoral component 106 includes a bone-facing side 114 and an opposite articular side 116. The bone-facing side 114 is configured to be fixed against a resected distal femur, for example by bone cement, press fit, or bone growth onto/into the bone-facing side. The bone-facing side 114 may include multiple portions corresponding to conventional anterior, anterior chamfer, distal, posterior chamfer, and/or posterior femoral resections. The bone-facing side 114 may include a pedestal 118 and/or a socket 120. The pedestal 118 in this example is a rectangular feature that protrudes superiorly from the surrounding bone-facing side. The pedestal 118 provides structural support for the socket 120, which protrudes superiorly from the superior aspect of the pedestal. The socket 120 may include a hole 122 to receive a femoral intramedullary stem (not shown). Referring to FIG. 14, the socket 120 and hole 122 are shown oriented along a generally superior-inferior axis 107 which may correspond to the femoral anatomical axis, also referred to as the femoral shaft axis. The articular side 116 is configured to articulate against a complementary articular side 184 of the tibial prosthesis 104, or against a natural articular surface of the proximal tibia. The articular side 116 may wrap around the anterior, distal, and posterior aspects of the femoral component 106 to replicate some or all of the natural articular surfaces of the distal femur.

Figures 15, 16, 17, 18:
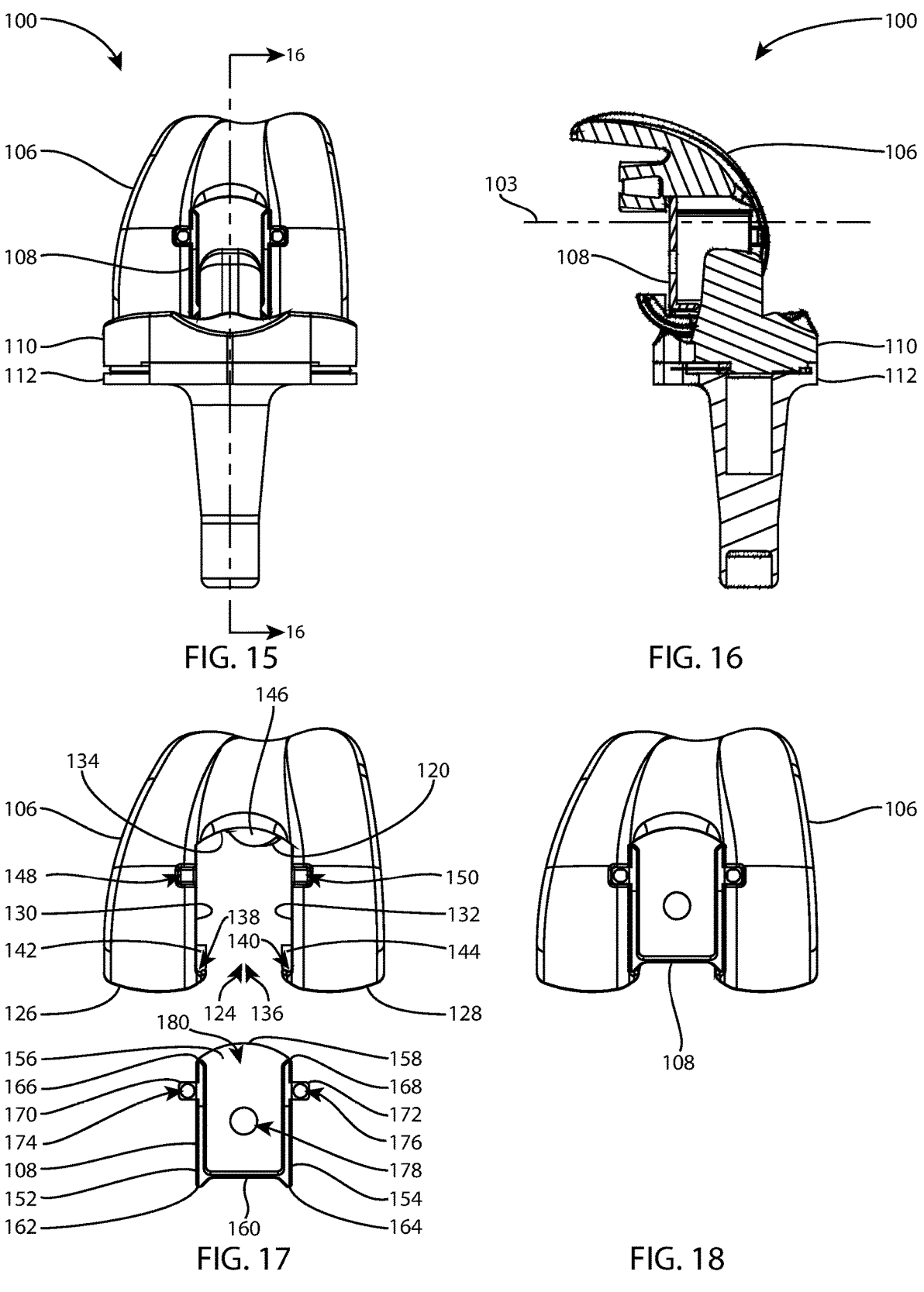
FIG. 15 is an anterior view of the knee arthroplasty system of FIG. 1, in flexion.
FIG. 16 is a cross-sectional view of the knee arthroplasty system of FIG. 15, taken along section line 16-16 of FIG. 15.
FIG. 17 is an anterior exploded view of the femoral component and adapter of the knee arthroplasty system of FIG. 15.
FIG. 18 is an anterior view of the assembled femoral component and adapter of the knee arthroplasty system of FIG. 15.

The femoral component 106 includes a receptacle 124, or space or alcove, which extends proximally into the distal aspect of the femoral component between the medial and lateral condyles 126, 128. The receptacle 124 receives the adapter 108 or the adapter 308. Referring to FIG. 12, the receptacle 124 is shown extending along a direction that is parallel to the axis 103. Referring to FIG. 17, the receptacle 124 has a non-circular cross-sectional shape perpendicular to the axis 103. A substantially rectangular cross-sectional shape is shown, although any shape that resists rotation about the axis 103 may be used. More specifically, in this example, the receptacle 124 has planar medial and lateral walls 130, 132, an arcuate anterior wall 134, and a substantially open posterior aspect 136 with medial and lateral posterior grooves 138, 140 that are shown extending parallel to the axis 103. In other examples, there may also be medial and lateral anterior grooves so that together, the medial posterior and anterior grooves form a medial undercut channel, and the lateral posterior and anterior grooves form a lateral undercut channel. Examples of undercut channels include dovetail channels, T-slots, and the like. The receptacle 124 may include one or more insertion stop features which prevent over-insertion of the adapter 108 or 308 into the receptacle. Medial and lateral posterior-superior insertion stop features 142, 144 are shown at the superior ends of the medial and lateral posterior grooves 138, 140. Another insertion stop feature 146 may be formed by the inferior side of the socket 120. Medial and lateral slots 148, 150 extend superiorly into the distal aspect of the femoral component 106 a short distance along the medial and lateral walls 130, 132. The superior walls of the slots 148, 150 may function as insertion stops.

The adapter 108 is received in the receptacle 124 of the femoral component 106 along a direction from the articular side 116 toward the bone-facing side 114. This means that the adapter 108 may be inserted into, fixed within, and removed from the receptacle 124 while the femoral component 106 is fixed to the distal femur, during the initial surgical procedure or during a subsequent surgical procedure. In this example, the adapter 108 is inserted along a distal-to-proximal direction parallel to the axis 103. However, the adapter 108 may be inserted along other directions, such as anterior-to-posterior perpendicular to the axis 103 as discussed below, or along oblique directions, such as distal-anterior to proximal-posterior at a 45 degree angle to the axis 103. The adapter insertion direction may be based upon the particular characteristics of the joint and arthroplasty prosthesis.

The adapter 108 has an exterior shape which is complementary to the shape of the receptacle 124. Referring to FIG. 17, the adapter 108 has a non-circular exterior cross-sectional shape perpendicular to the axis 103. A substantially rectangular cross-sectional shape is shown, although any shape that resists rotation about the axis 103 may be used. More specifically, in this example, the adapter 108 has planar medial and lateral walls 152, 154, a planar superior wall 156 with an arcuate anterior border 158, and a planar posterior wall 160 with medial and lateral posterior ridges 162, 164 that are shown extending parallel to the axis 103. The distal and anterior aspects are open. This example also includes medial and lateral anterior ridges 166, 168 so that together, the medial posterior and anterior ridges 162, 166 form a medial undercut rail, and the lateral posterior and anterior ridges 164, 168 form a lateral undercut rail. Examples of undercut rails include dovetail rails, T-rails, and the like. The adapter 108 may include one or more insertion stop features which prevent over-insertion of the adapter into the receptacle 124. The superior ends of the medial and lateral posterior ridges 162, 164 may function as insertion stops against the medial and lateral posterior-superior insertion stop features 142, 144 of the femoral component 106, and the superior wall 156 in the vicinity of the arcuate anterior border 158 may function as an insertion stop against the inferior side of the socket 120. The adapter 108 may include medial and lateral protrusions 170, 172 which extend outwardly medially from the medial wall 152 and laterally from the lateral wall 154, respectively. The superior sides of the protrusions 170, 172 may function as insertion stops against the superior walls of the slots 148, 150. The protrusions 170, 172 may include through holes 174, 176 which extend along a superior-inferior direction. The holes 174, 176 may receive fasteners (not shown). A hole 178 may extend through the superior wall 156 along the superior-inferior direction. The hole 178 may engage an adapter insertion and/or removal tool (not shown). The walls 152, 154, 156, 160 define an interior cavity 180 or space, which may be substantially rectangular. The cavity 180 may be referred to as a constraint feature. The cavity 180 may include a cam for interaction with the second articular portion 190 of the tibial articular insert 110, described below.

Figure 2:
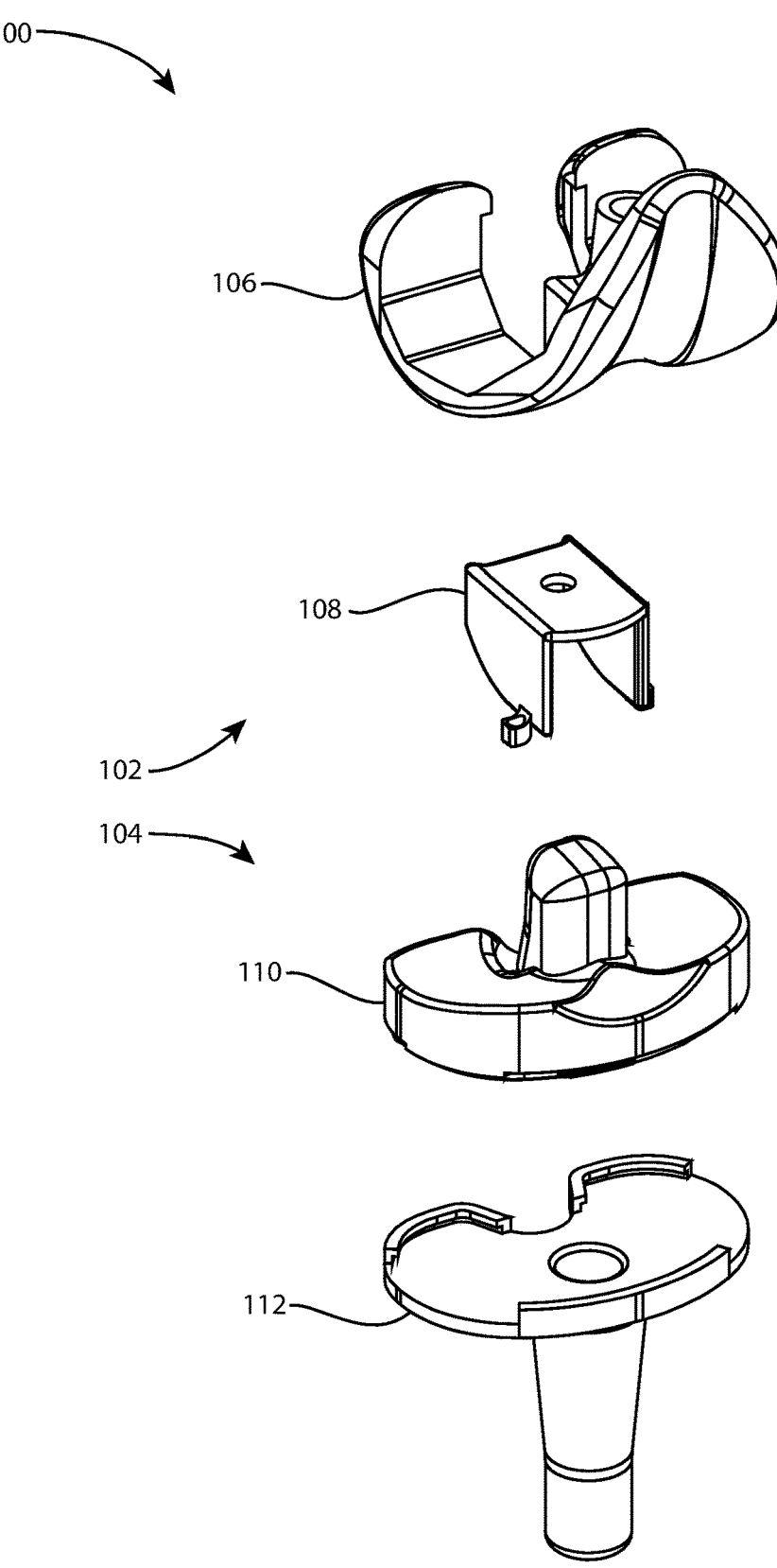
FIG. 2 is an oblique exploded view of the knee arthroplasty system of FIG. 1.
Figures 3, 4:
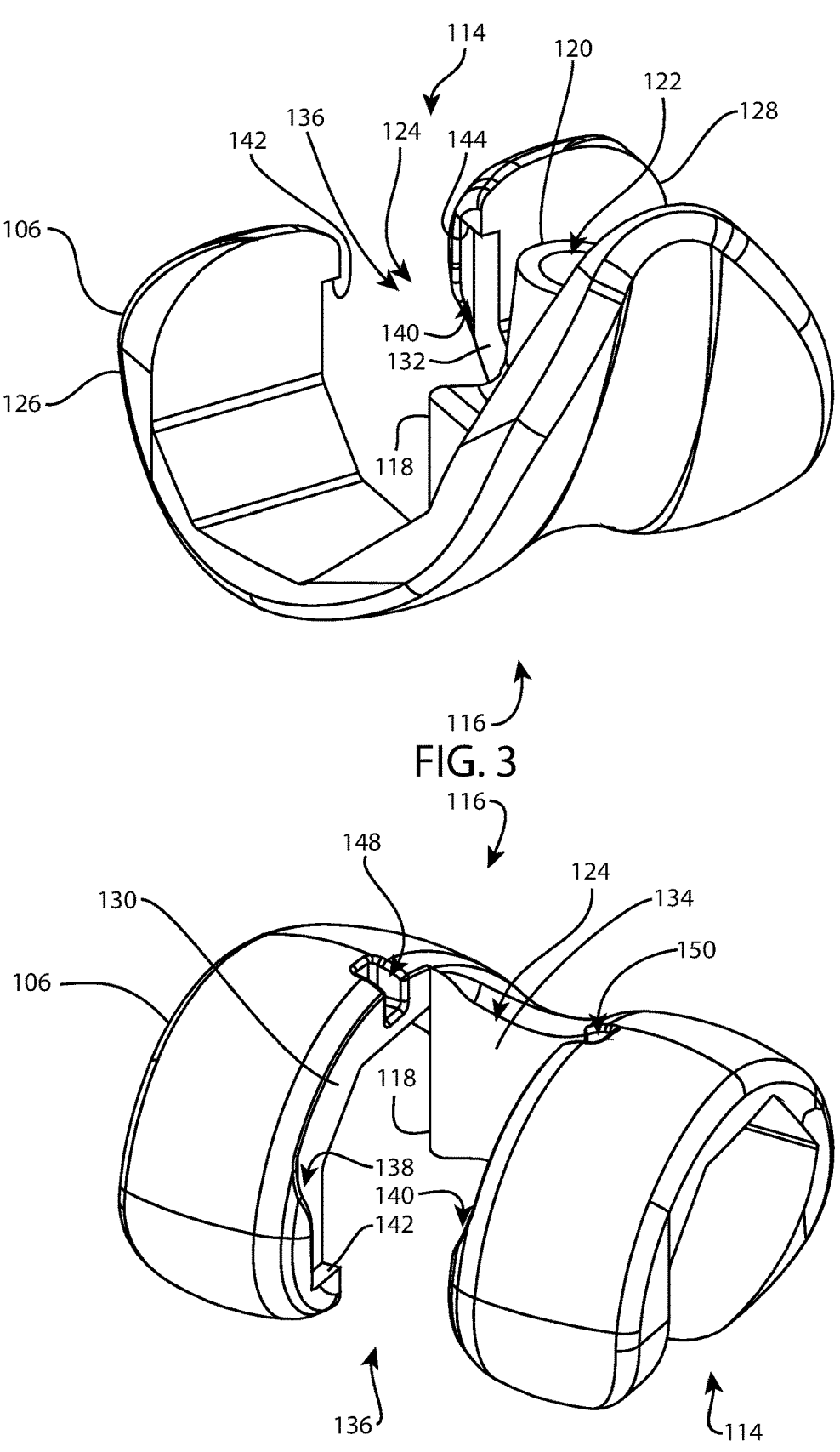
FIG. 3 is an oblique view of a femoral component of the knee arthroplasty system of FIG. 1.
FIG. 4 is another oblique view of the femoral component of FIG. 3, from a different direction.
Figure 5:
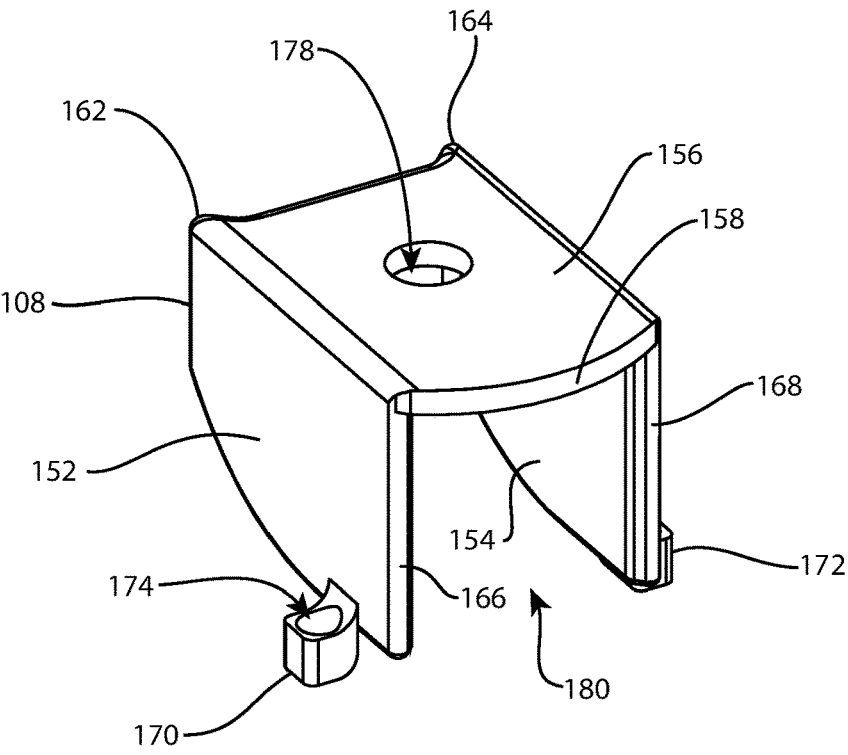
FIG. 5 is an oblique view of an adapter of the knee arthroplasty system of FIG. 1.
Figure 6:
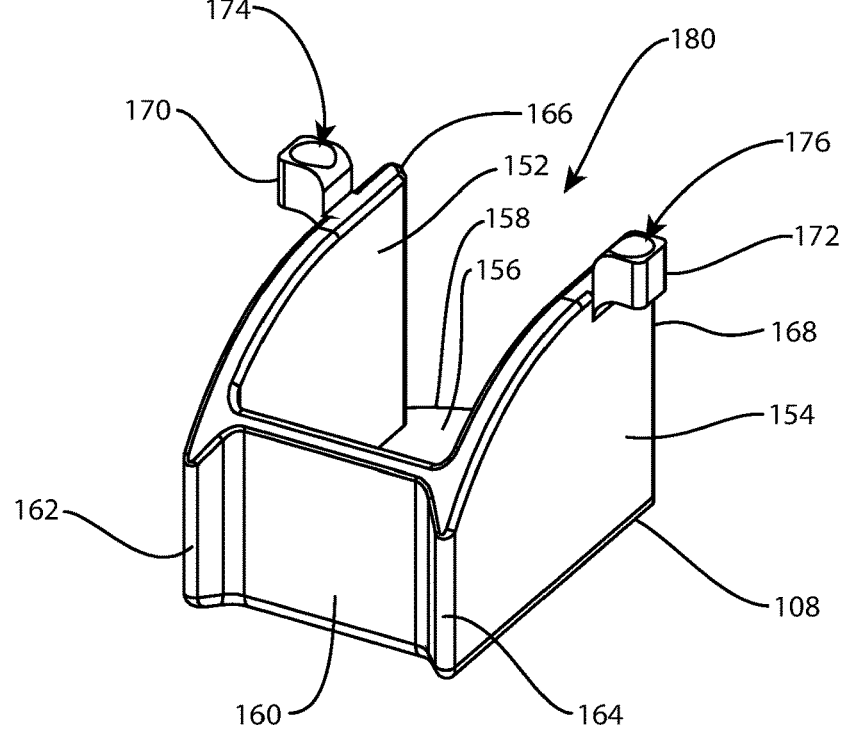
FIG. 6 is another oblique view of the adapter of FIG. 5, from a different direction.
Figure 7:
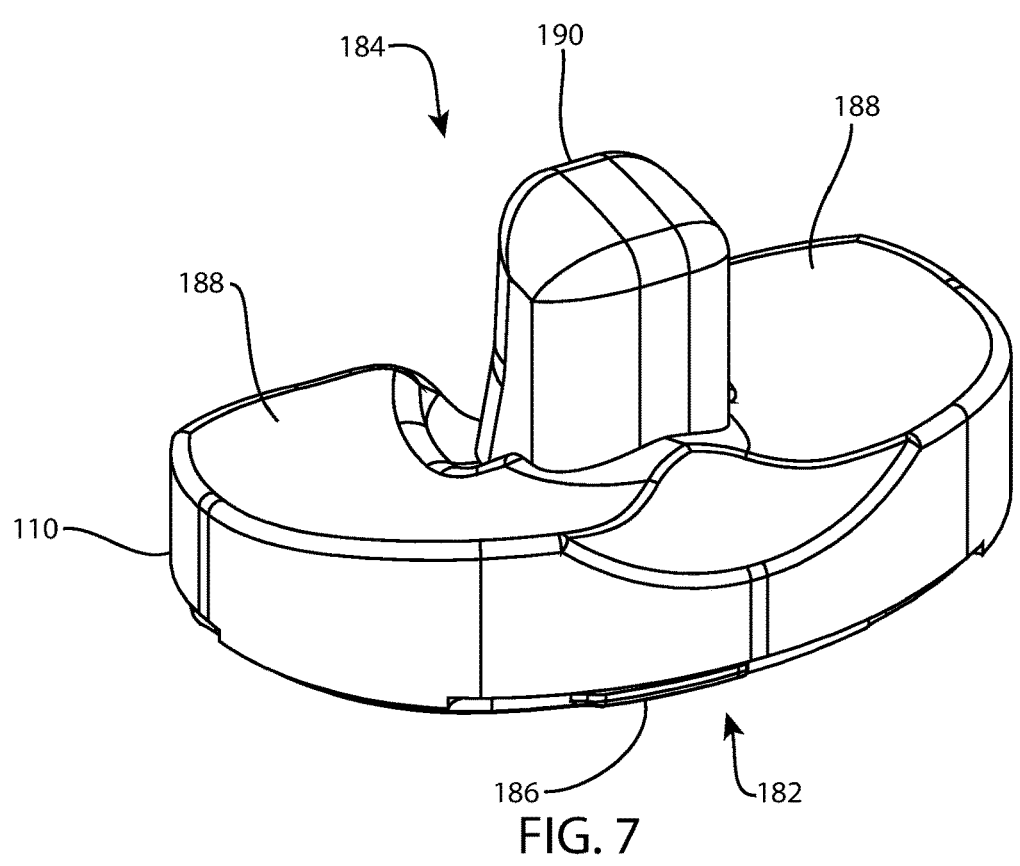
FIG. 7 is an oblique view of a tibial articular insert of the knee arthroplasty system of FIG. 1.
Figure 8:
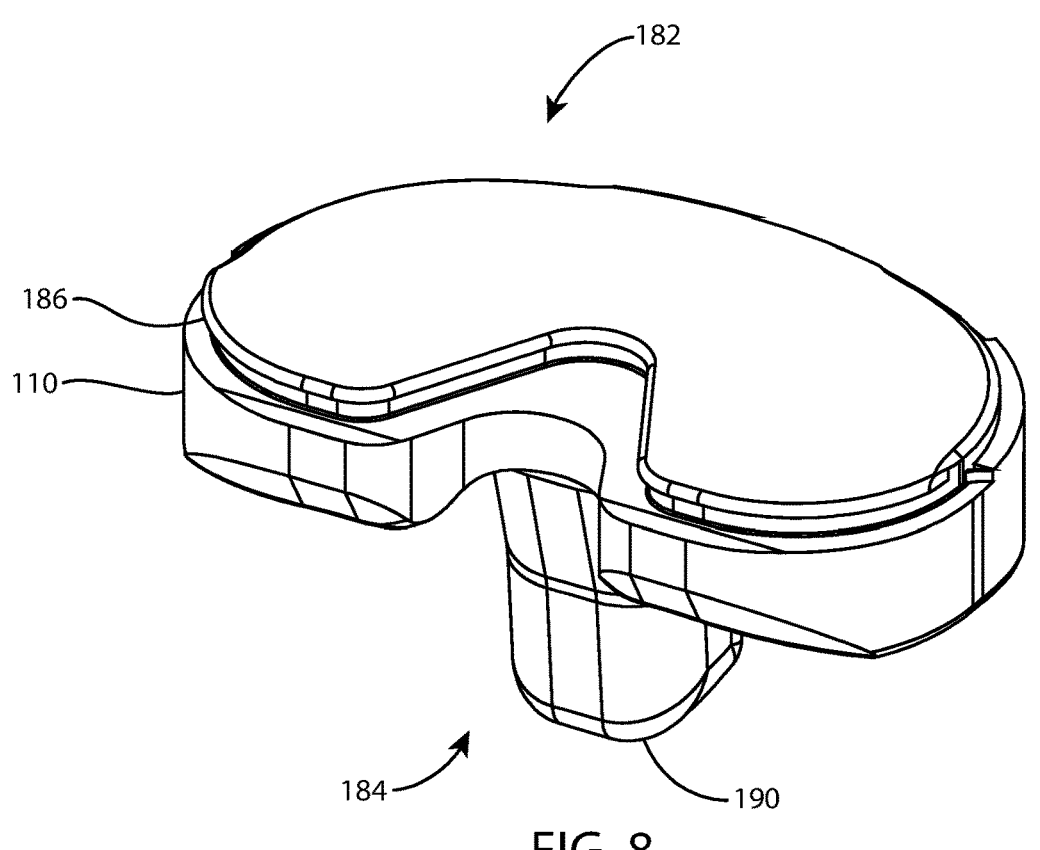
FIG. 8 is another oblique view of the tibial articular insert of FIG. 7, from a different direction.

The femoral prosthesis 102 may be assembled by orienting the adapter 108 relative to the femoral component 106 as shown in FIG. 2; sliding the adapter into the receptacle 124; sliding the medial and lateral protrusions 170, 172 into the medial and lateral slots 148, 150 until at least one adapter insertion stop feature contacts a femoral component insertion stop feature; and fixing the adapter to the femoral component. The adapter 108 may slide into the receptacle along a direction from the articular side 116 toward the bone-facing side 114, which in this example is from distal to proximal. The protrusions 170, 172 may slide into the slots 148, 150 along the same direction. The adapter 108 may be fixed to the femoral component 106 by inserting fasteners (not shown) through the holes 174, 176 of the protrusions 170, 172 and into the superior walls of the slots 148, 150. The protrusions 170, 172, holes 174, 176, and slots 148, 150 may thus be referred to as removal stop features which prevent unintentional removal of the adapter from the receptacle, in combination with the fasteners. The removal stop features may be disengaged by removing the fasteners.

When the femoral prosthesis 102 is assembled, the femoral component 106 and the adapter 108 are fixed together. The adapter is insertable into, fixable within, and removable from the receptacle 124 when the femoral prosthesis 102 is fixed to a distal femur. The adapter is interchangeable with other distal adapters, such as adapter 308 discussed below.

The tibial articular insert 110 includes a bone-facing side 182 and an opposite articular side 184. The bone-facing side 182 is configured to be coupled to the tibial baseplate 112, and may be referred to as a baseplate-facing side or a distal side. The bone-facing side 182 may include a locking feature 186 to fix the tibial articular insert 110 to the tibial baseplate 112, although mobile bearing configurations are also contemplated. The articular side 184 may include a first articular portion 188 for articulation against the articular side 116 of the femoral component 106. The first articular portion 188 may replicate the natural medial and lateral tibial articular condyles. The articular side 184 may also include a second articular portion 190, which in this example may protrude proximally from the first articular portion 188. The second articular portion 190 may be referred to as a constraint feature. The second articular portion 190 in this example is for articulation within the cavity 180 of the adapter 108.

The tibial baseplate 112 includes a bone-facing side 192 and an opposite superior side 194. The bone-facing side 192 is configured to be fixed against a resected proximal tibia, for example by bone cement, press fit, or bone growth onto/into the bone-facing side. The bone-facing side 192 may include a distally protruding boss 196 which may include a hole 198 to receive a tibial intramedullary stem 30 (not shown). The superior side 194 is configured to be coupled to the tibial articular insert 110. The superior side 194 may include a locking feature 200 which is complementary to the locking feature 186 of the tibial articular insert 110, although mobile bearing configurations are also contemplated. A hole 202 may extend distally into the boss 196. The hole 202 may or may not intersect the hole 198.

The tibial prosthesis 104 may be assembled by orienting the tibial baseplate 112 relative to the tibial articular insert 110 as shown in FIG. 2; and coupling the tibial baseplate 112 to the tibial articular insert 110. Coupling the tibial baseplate 112 to the tibial articular insert 110 may include engaging the locking features 186, 200 to fix the tibial baseplate 112 to the tibial articular insert 110.

When the tibial prosthesis 104 is assembled, the tibial articular insert 110 and the tibial baseplate 112 may be fixed together. The tibial articular insert 110 may be removably fixed to the tibial baseplate 112. A mobile bearing tibial articular insert is also contemplated, in which case the tibial articular insert 110 is free to move relative to the tibial baseplate 112 in use, at least within a limited range of motion.

The knee arthroplasty system 100 may be assembled by orienting the femoral prosthesis 102 relative to the tibial prosthesis 104 as shown in FIG. 1; and bringing the femoral and tibial prostheses 102, 104 together so that the first articular portion 188 of the tibial articular insert 110 is against the articular side 116 of the femoral component 106 and the second articular portion 190 of the tibial articular insert 110 is received in the cavity 180 of the adapter 108.

When the knee arthroplasty system 100 is assembled, the tibial prosthesis 104 articulates against the femoral prosthesis 102 to provide a range of motion between the tibial and femoral prostheses. The second articular portion 190 of the tibial articular insert 110 articulates within the cavity 180 of the adapter 108 to modify the nominal range of motion that would be possible if the second articular portion 190 was absent. The knee arthroplasty system 100 has enhanced stability in use compared to a design that lacks the CCK constraint features of the second articular portion 190 and the cavity 180. More specifically, with reference to FIGS. 11-14, when the knee arthroplasty system 100 is in extension, the tibial prosthesis 104 has limited translation relative to the femoral prosthesis 102 along directions that are perpendicular to the axis 103. Specifically, FIG. 12 shows that the tibial prosthesis 104 has limited anterior-posterior translation and FIG. 14 shows that the tibial prosthesis has limited medial-lateral translation. With reference to FIGS. 15 and 16, when the knee arthroplasty system 100 is in flexion, the tibial prosthesis 104 has limited translation along a direction that is parallel to the axis 103. Specifically, FIG. 16 shows that the tibial prosthesis 104 has limited superior translation. The tibial prosthesis 104 also has limited medial-lateral translation in flexion.

With reference to FIGS. 15-18, the adapter 108 is insertable into, fixable within, and removable from the receptacle 124 along a direction that is parallel to the axis 103, from the distal articular side 116 toward the proximal bone-facing side 114, while the femoral prosthesis 102 is fixed to a distal femur. The adapter 108 is interchangeable with other distal adapters, such as adapter 308. Adapters can be exchanged before or after the femoral component 106 is fixed to the distal femur, even in a subsequent surgery.

A surgical method of implanting the knee arthroplasty system 100 may include some or all of the following steps in any order.

Preparing the distal femur may include making anterior, anterior chamfer, distal, posterior chamfer, and posterior resections to complement the bone-facing side 114 of the femoral component 106; drilling a hole to receive the socket 120, with or without a femoral intramedullary stem (not shown); and/or making a box cut to receive the pedestal 118 and/or adapter 108.

Fixing the femoral component 106 to the distal femur may include applying bone cement to the distal femur and/or the bone-facing side 114 of the femoral component 106, or press-fitting the femoral component 106 to the distal femur. Fasteners may be used to fix the femoral component to the distal femur.

Fixing the adapter 108 to the femoral component 106 may include flexing the knee; sliding the adapter into the receptacle 124 from distal to proximal; sliding the medial and lateral protrusions 170, 172 into the medial and lateral slots 148, 150; and fixing the adapter to the femoral component. Fasteners may be used to fix the adapter to the femoral component.

Preparing the proximal tibia may include making a proximal tibial resection to complement the bone-facing side 192 of the tibial baseplate 112; and drilling a hole to receive the boss 196, with or without a tibial intramedullary stem (not shown).

Fixing the tibial baseplate 112 to the proximal tibia may include applying bone cement to the proximal tibia and/or the bone-facing side 192 of the tibial baseplate 112, or press-fitting the tibial baseplate 112 to the proximal tibia. Fasteners may be used to fix the tibial baseplate to the proximal tibia.

Coupling the tibial articular insert 110 to the tibial baseplate may include fixing the tibial articular insert to the tibial baseplate, or engaging mobile bearing features of the tibial articular insert and the tibial baseplate.

A surgical method of revising the knee arthroplasty system 100 may include some or all of the following steps in any order. Placing a previously-operated knee joint in flexion; exposing the adapter 108; releasing the adapter from fixation to the femoral component 106; removing the adapter from the receptacle along a proximal-to-distal direction; inserting a different adapter into the receptacle along a distal-to-proximal direction; fixing the different adapter to the femoral component 106; and closing the incision. The tibial articular insert 110 may be disconnected from the tibial baseplate 112 to facilitate access to the adapter 108, and optionally reconnected after the different adapter has been fixed to the femoral component. The tibial articular insert 110 may be replaced with a different tibial articular insert during the same revision surgical procedure, for example to convert between CCK and hinged or fixed and mobile designs.

Figures 9, 10:
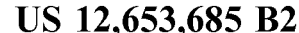
FIG. 9 is an oblique view of a tibial baseplate of the knee arthroplasty system of FIG. 1.
FIG. 10 is another oblique view of the tibial baseplate of FIG. 9, from a different direction.
Figure 19:
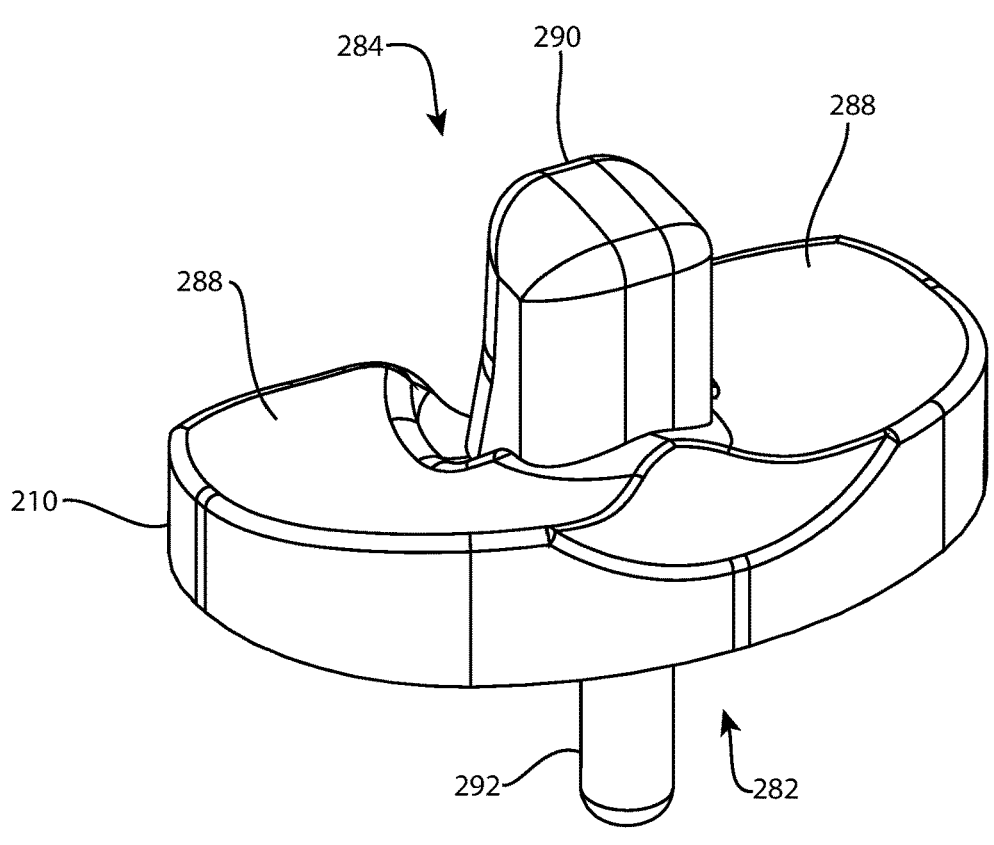
FIG. 19 is an oblique view of another tibial articular insert for use in the knee arthroplasty system of FIG. 1.
Figure 20:
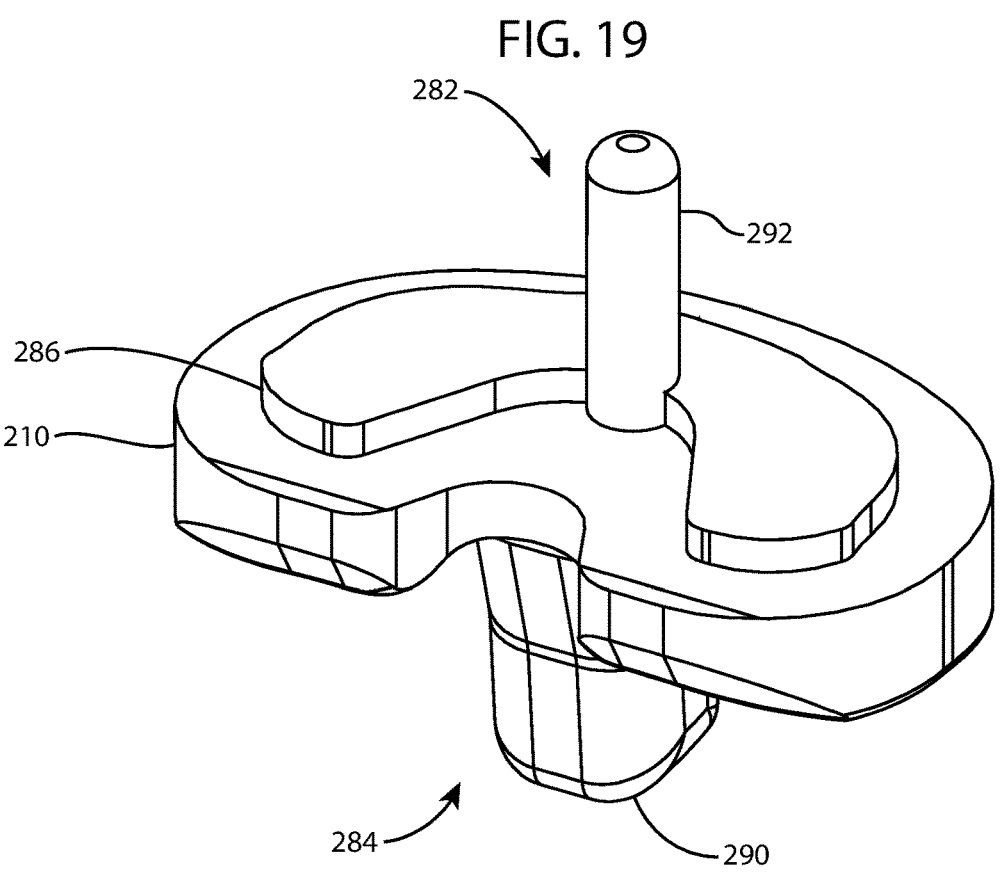
FIG. 20 is another oblique view of the tibial articular insert of FIG. 19, from a different direction.

Referring to FIGS. 19 and 20, another tibial articular insert 210 for use in the knee arthroplasty system 100 is shown. The tibial articular insert 210 may be referred to as a mobile bearing design, and may be used interchangeably with the fixed tibial articular insert 110. The tibial articular insert 210 includes a bone-facing side 282 and an opposite articular side 284. The bone-facing side 282 is configured to be coupled to the tibial baseplate 112. The bone-facing side may include a mobile bearing feature 286 to permit limited translation and/or rotation of the tibial articular insert 210 relative to the tibial baseplate 112. The mobile bearing feature 286 in this example is a distal protrusion whose outer periphery is complementary to, and smaller than, the profile of the locking feature 200 of the tibial baseplate 112 (FIG. 9). The tibial articular insert 210 may also include a distal post 292 which extends distally from a central region of the bone-facing side. The post 292 may be referred to as a second mobile bearing feature. The articular side 284 may include a first articular portion 288 for articulation against the articular side 116 of the femoral component 106. The first articular portion 288 may replicate the natural medial and lateral tibial articular condyles. The articular side 284 may also include a second articular portion 290, which may protrude proximally from the first articular portion 288. The second articular portion 290 may be referred to as a constraint feature. The second articular portion 290 in this example is for articulation within the cavity 180 of the adapter 108. The first and second articular portions 288, 290 may be identical to the first and second articular portions 188, 190 of the tibial articular insert 110.

Referring to FIGS. 21-38, another knee arthroplasty system 300 may include a femoral prosthesis 302 and/or a tibial prosthesis 304. This embodiment may be referred to as a distal hinged fixed design. A left knee design is shown. The femoral prosthesis 302 may include the femoral component 106 and an adapter 308. The adapter 308 may be a subassembly of multiple parts. The femoral prosthesis 302 may include additional components, such as a femoral intramedullary stem (not shown) or defect-filling augments (not shown). Referring to FIGS. 31-34, axis 303 corresponds to the femoral mechanical axis. The tibial prosthesis 304 may include a tibial articular insert 310 and the tibial baseplate 112, or the tibial articular insert and tibial baseplate may be integrally formed as a single component. The tibial prosthesis 304 may include additional components, such as an intramedullary stem (not shown) or defect-filling augments (not shown).

Figure 22:
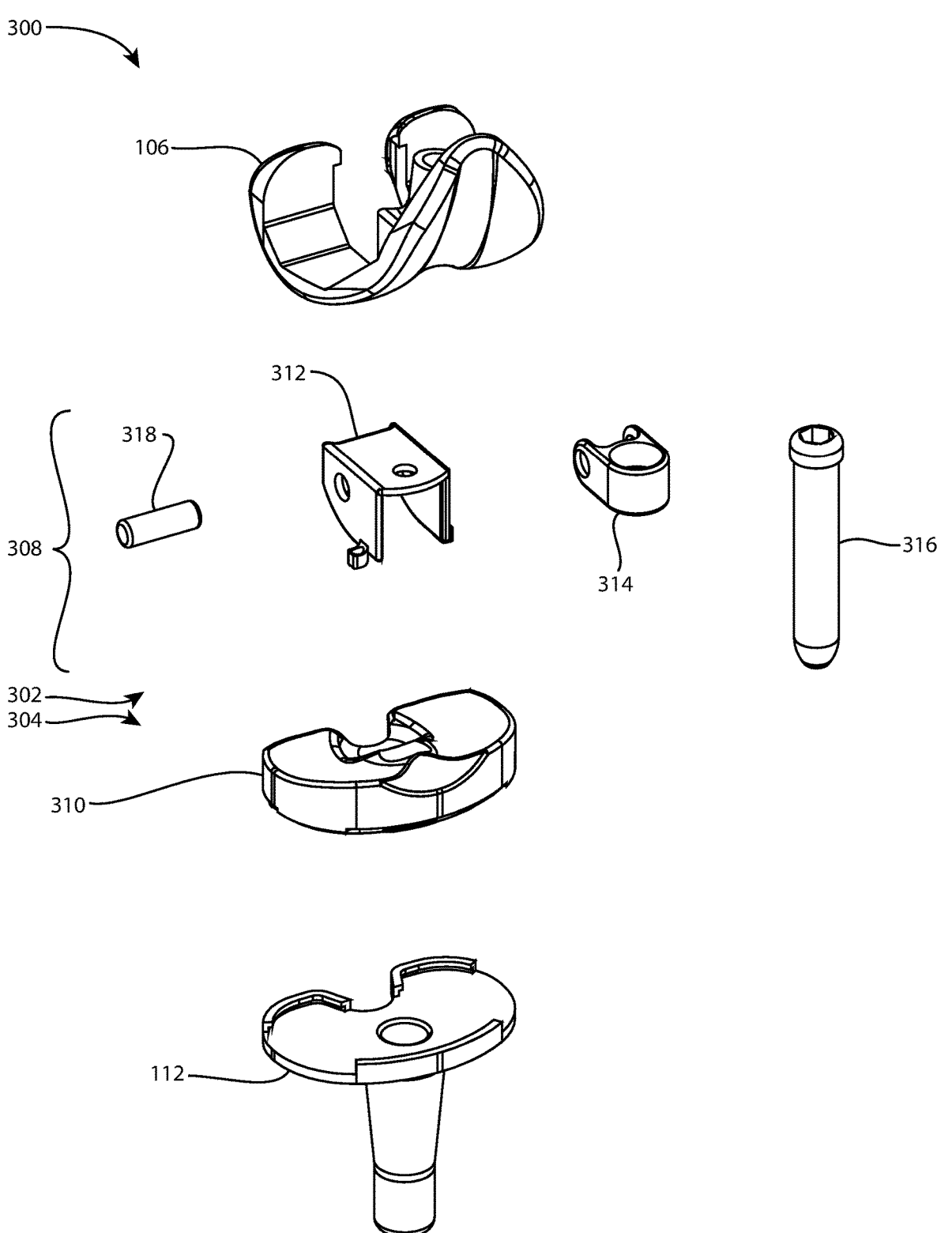
FIG. 22 is an oblique exploded view of the knee arthroplasty system of FIG. 21.

Referring to FIG. 22, the adapter 308 may include an adapter body 312, a sleeve 314, a post 316, and a pin 318. The adapter 308 is received in the receptacle 124 of the femoral component 106 along a direction from the articular side 116 toward the bone-facing side 114. This means that the adapter 308 may be inserted into, fixed within, and removed from the receptacle 124 while the femoral component 106 is fixed to the distal femur, during the initial surgical procedure or during a subsequent surgical procedure. In this example, the adapter 308 is inserted along a distal-to-proximal direction parallel to the axis 303. However, the adapter 308 may be inserted along other directions, such as anterior-to-posterior perpendicular to the axis 303 as discussed below, or along oblique directions, such as distal-anterior to proximal-posterior at a 45 degree angle to the axis 303. The adapter insertion direction may be based upon the particular characteristics of the joint and arthroplasty prosthesis.

Figure 23:
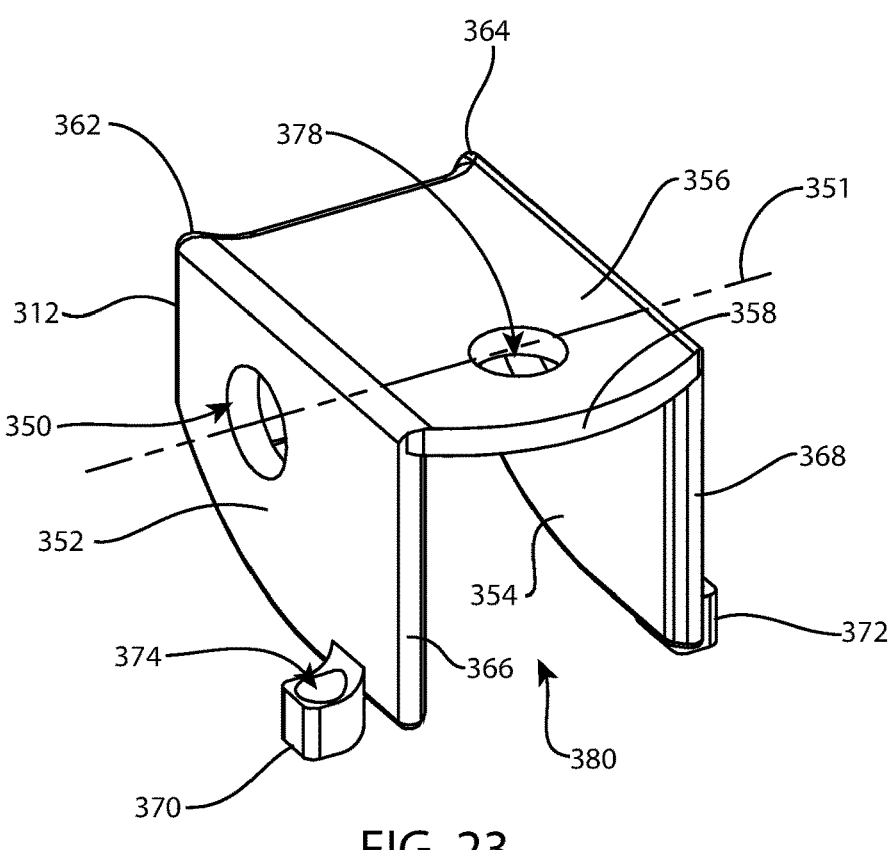
FIG. 23 is an oblique view of an adapter body of the knee arthroplasty system of FIG. 21.
Figure 24:
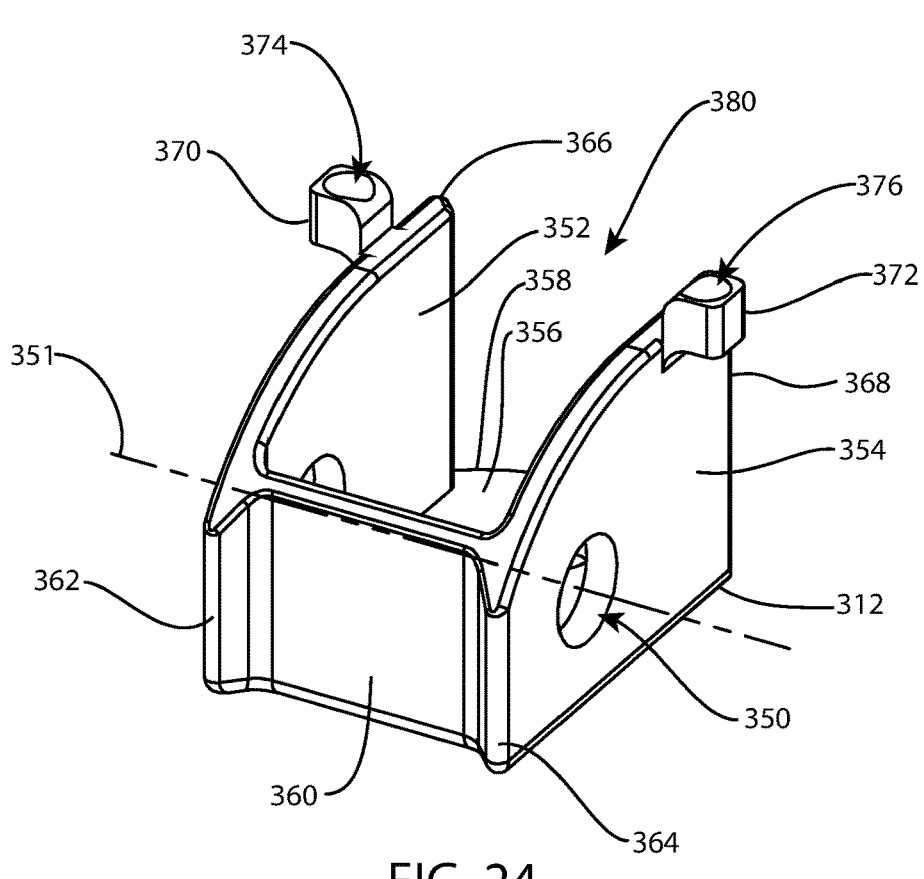
FIG. 24 is another oblique view of the adapter body of FIG. 23, from a different direction.
Figures 37, 38:
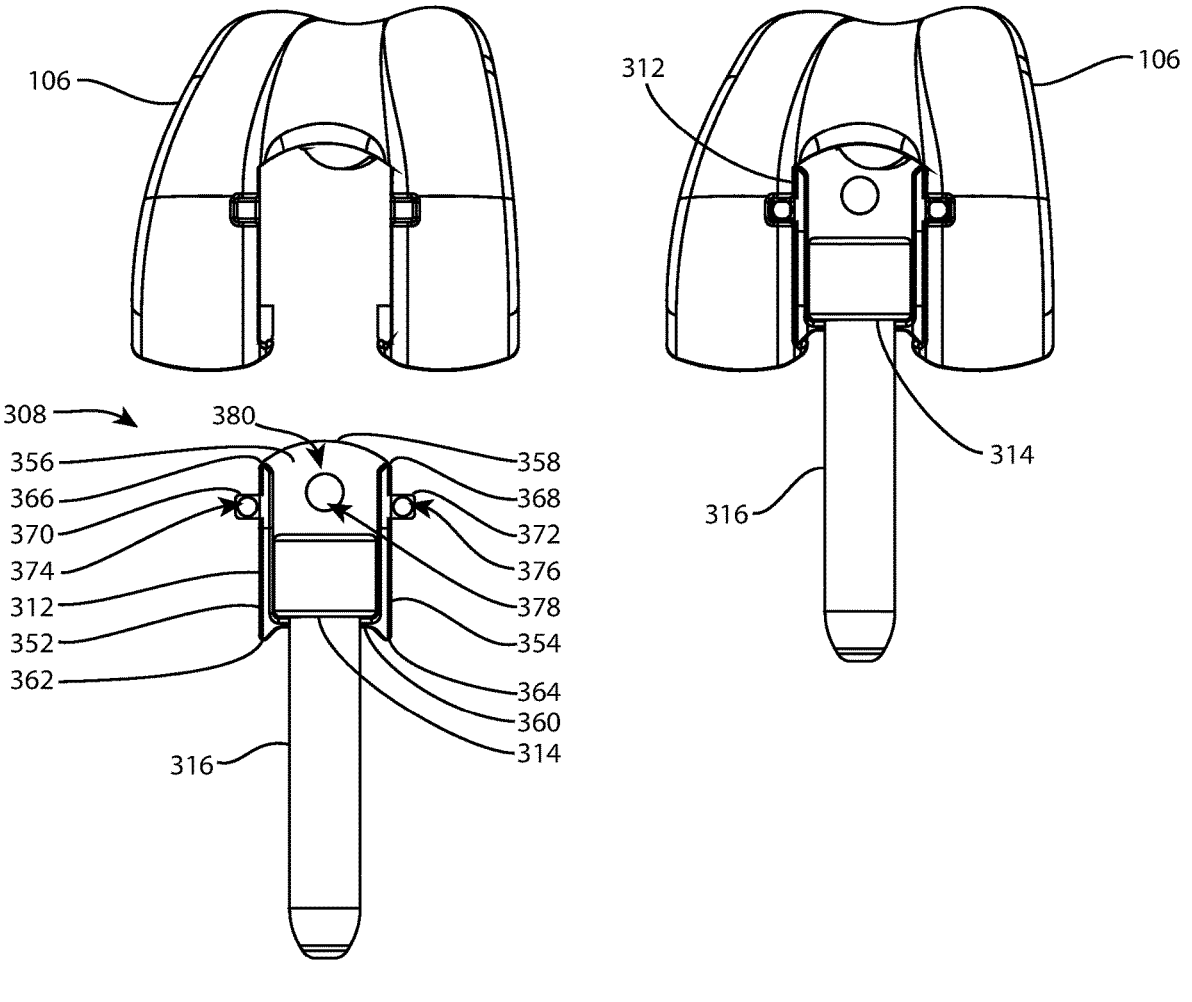
FIG. 37 is an anterior exploded view of the femoral component and adapter of the knee arthroplasty system of FIG. 35.
FIG. 38 is an anterior view of the assembled femoral component and adapter of the knee arthroplasty system of FIG. 35.

The adapter body 312 has an exterior shape which is complementary to the shape of the receptacle 124. Referring to FIG. 37, the adapter body 312 has a non-circular exterior cross-sectional shape perpendicular to the axis 303. A substantially rectangular cross-sectional shape is shown, although any shape that resists rotation about the axis 303 may be used. Referring to FIGS. 23-24, in this example, the adapter body 312 has planar medial and lateral walls 352, 354, a planar superior wall 356 with an arcuate anterior border 358, and a planar posterior wall 360 with medial and lateral posterior ridges 362, 364 that are shown extending parallel to the axis 303. The distal and anterior aspects are open. This example also includes medial and lateral anterior ridges 366, 368 so that together, the medial posterior and anterior ridges 362, 366 form a medial undercut rail, and the lateral posterior and anterior ridges 364, 368 form a lateral undercut rail. Examples of undercut rails include dovetail rails, T-rails, and the like. The adapter body 312 may include one or more insertion stop features which prevent over-insertion of the adapter into the receptacle 124. The superior ends of the medial and lateral posterior ridges 362, 364 may function as insertion stops against the medial and lateral posterior-superior insertion stop features 142, 144 of the femoral component 106, and the superior wall 356 in the vicinity of the arcuate anterior border 358 may function as an insertion stop against the inferior side of the socket 120. The adapter body 312 may include medial and lateral protrusions 370, 372 which extend outwardly medially from the medial wall 352 and laterally from the lateral wall 354, respectively. The superior sides of the protrusions 370, 372 may function as insertion stops against the superior walls of the slots 148, 150. The protrusions 370, 372 may include through holes 374, 376 which extend along a superior-inferior direction. The holes 374, 376 may receive fasteners (not shown). A hole 378 may extend through the superior wall 356 along the superior-inferior direction. The hole 378 may engage an adapter insertion and/or removal tool (not shown). The walls 352, 354, 356, 360 define an interior cavity 380 or space, which may be substantially rectangular. The cavity 380 may be referred to as a constraint feature. A hole 350 may extend through the adapter body 312 along a medial-lateral direction to establish a hinge axis 351 which is perpendicular to the axis 303. The hole 350 receives the pin 318.

Figures 25, 26, 27, 28:
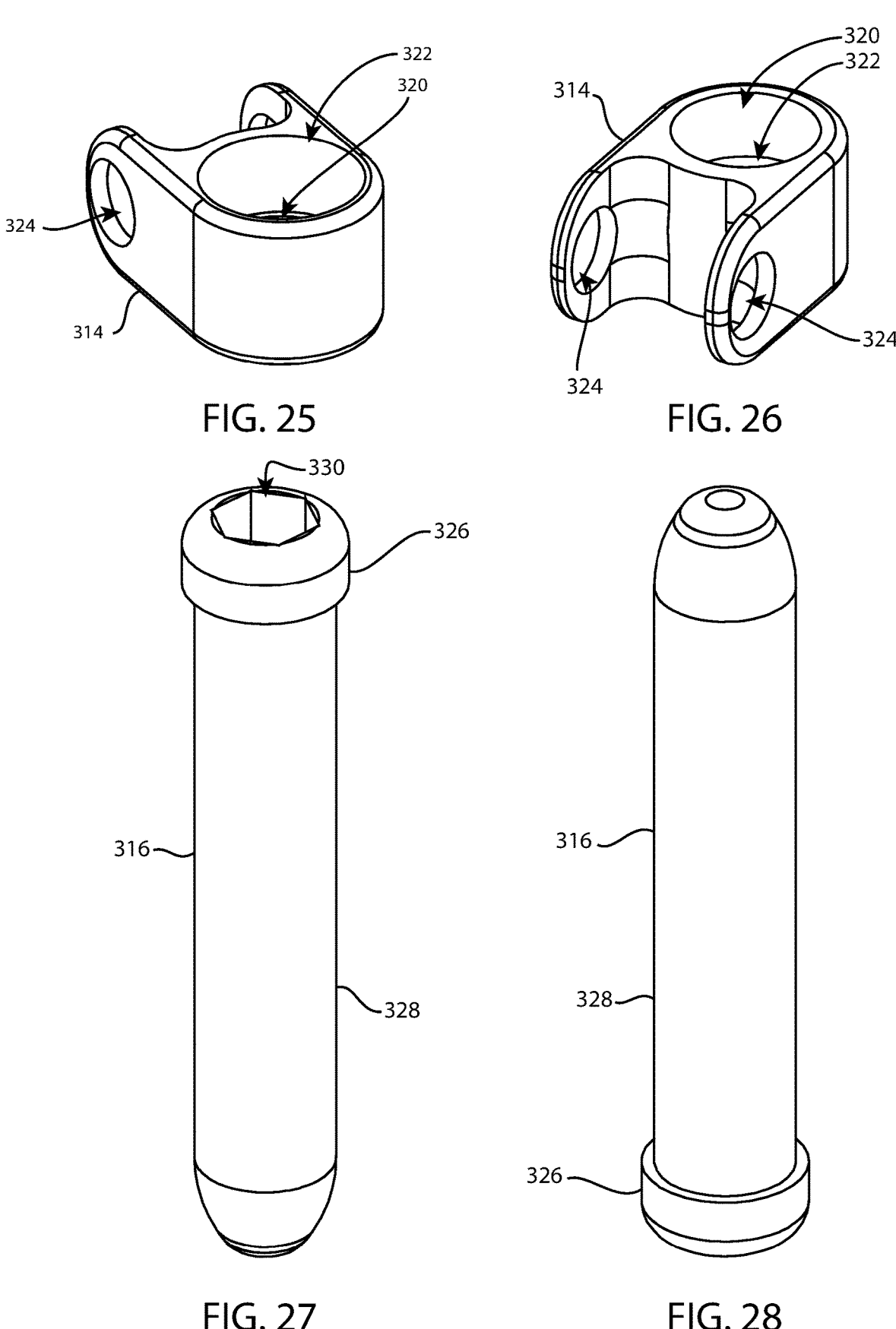
FIG. 25 is an oblique view of a sleeve of the knee arthroplasty system of FIG. 21.
FIG. 26 is another oblique view of the sleeve of FIG. 25, from a different direction.
FIG. 27 is an oblique view of a post of the knee arthroplasty system of FIG. 21.
FIG. 28 is another oblique view of the post of FIG. 27, from a different direction.
Figure 29:
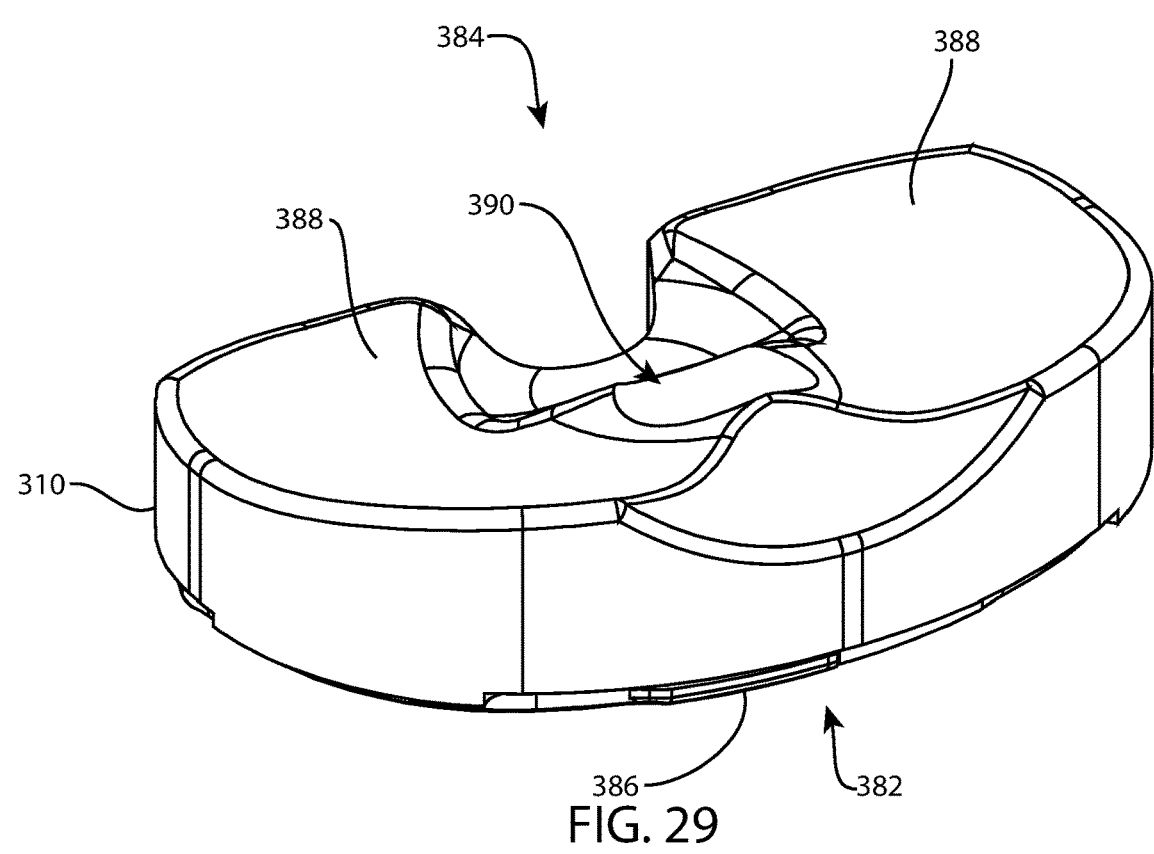
FIG. 29 is an oblique view of a tibial articular insert of the knee arthroplasty system of FIG. 21.
Figure 30:
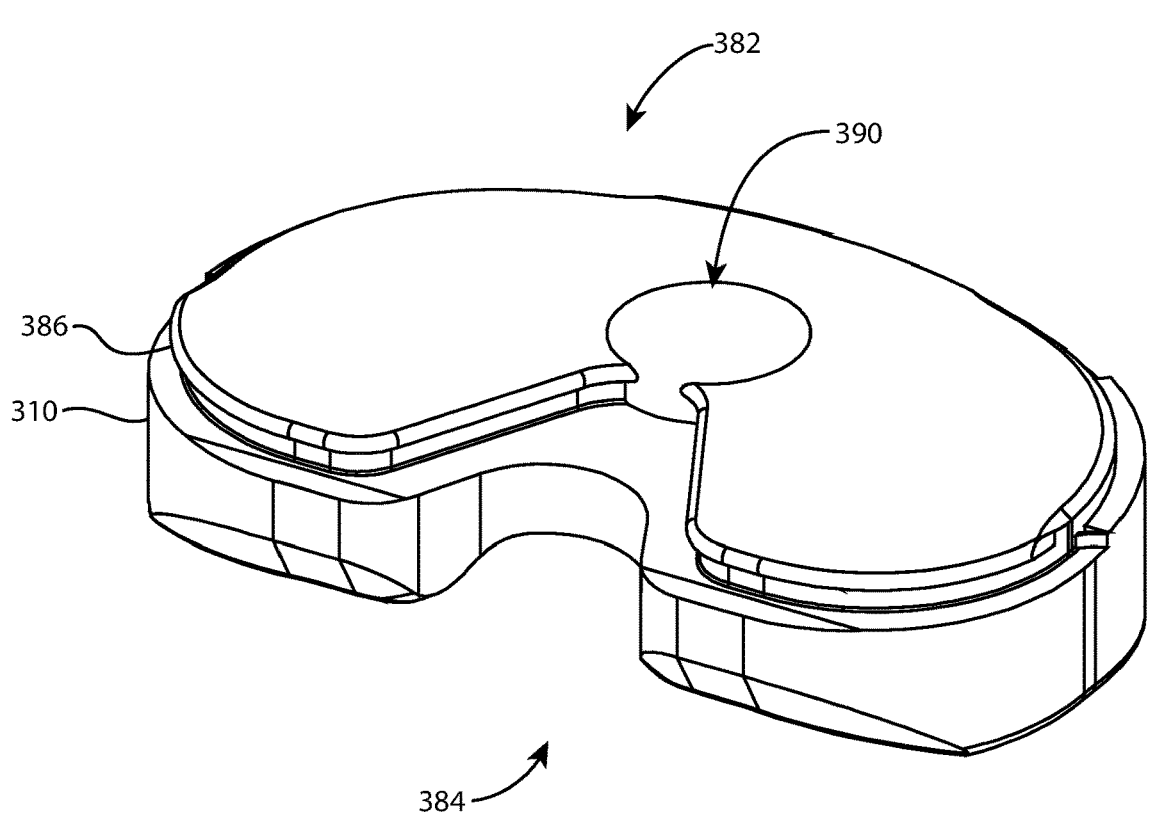
FIG. 30 is another oblique view of the tibial articular insert of FIG. 29, from a different direction.

Referring to FIGS. 25-26, the sleeve 314 includes a superior-inferior through bore 320, which may include a superior counterbore 322. The bore 320 and/or counterbore 322 may include internal threads or other means to fix the head 326 of the post 316 to the sleeve 314. The sleeve 314 also includes a medial-lateral through hole 324 which is posterior to the bore 320 and counterbore 322. The hole 324 receives the pin 318.

Referring to FIGS. 27-28, the post 316 includes a proximal head 326 and a distal shaft 328. The head 326 may be externally threaded to engage internal threads of the sleeve 314, and may include a torque fitting 330, such as the hex socket shown. The distal tip of the shaft 328 may taper to a blunt distal end.

The adapter 308 may be assembled by orienting the sleeve 314 relative to the adapter body 312 as shown in FIG. 22; inserting the sleeve into the cavity 380 so that the holes 350, 324 are aligned and the holes 378, 320 are aligned; inserting the pin 318 through the holes 350, 324 so that the sleeve 314 is free to rotate relative to the adapter body 312 about the hinge axis 351; orienting the post 316 relative to the sleeve 314 as shown in FIG. 22; and fixing the head 326 of the post 316 in the bore 320 and/or counterbore 322 of the sleeve 314 so that the shaft 328 of the post 316 protrudes distally from the bore 320. The adapter 308 may be provided in a partially assembled state with the adapter body 312, the sleeve 314, and the pin 318 coupled together, with the step of fixing the head 326 of the post 316 in the bore 320 and/or counterbore 322 of the sleeve 314 performed during the surgical procedure.

When the adapter 308 is assembled, the fixed-together sleeve 314 and post 316 are free to rotate relative to the adapter body 312 about the hinge axis 351.

The femoral prosthesis 302 may be assembled by orienting the adapter body 312 relative to the femoral component 106 as shown in FIG. 22, the adapter body 312 preferably coupled to at least the sleeve 314 and the pin 318; sliding the adapter body into the receptacle 124; sliding the medial and lateral protrusions 370, 372 into the medial and lateral slots 148, 150 until at least one adapter insertion stop feature contacts a femoral component insertion stop feature; fixing the adapter body to the femoral component; orienting the post 316 relative to the sleeve 314 as shown in FIG. 22; and fixing the head 326 of the post 316 in the bore 320 and/or counterbore 322 of the sleeve 314 so that the shaft 328 of the post 316 protrudes distally from the bore 320. The adapter body 312 may slide into the receptacle 124 along a direction from the articular side 116 toward the bone-facing side 114, which in this example is from distal to proximal. The protrusions 370, 372 may slide into the slots 148, 150 along the same direction. The adapter body 312 may be fixed to the femoral component 106 by inserting fasteners (not shown) through the holes 374, 376 of the protrusions 370, 372 and into the superior walls of the slots 148, 150. The protrusions 370, 372, holes 374, 376, and slots 148, 150 may thus be referred to as removal stop features which prevent unintentional removal of the adapter 308 from the receptacle, in combination with the fasteners. The removal stop features may be disengaged by removing the fasteners. The step of fixing the head 326 of the post 316 in the bore 320 and/or counterbore 322 of the sleeve 314 may be performed during surgery after the tibial baseplate 112 has been fixed to the resected proximal tibia.

When the femoral prosthesis 302 is assembled, the femoral component 106 and the adapter body 312 are fixed together, and the sleeve 314 and post 316 (if attached) are free to rotate relative to the adapter body 312 about the hinge axis 351. The adapter body 312 is insertable into, fixable within, and removable from the receptacle 124 when the femoral prosthesis 302 is fixed to a distal femur. The adapter 308 is interchangeable with other distal adapters, such as adapter 108.

The tibial articular insert 310 includes a bone-facing side 382 and an opposite articular side 384. The bone-facing side 382 is configured to be coupled to the tibial baseplate 112, and may be referred to as a baseplate-facing side or a distal side. The bone-facing side 382 may include a locking feature 386 to fix the tibial articular insert 310 to the tibial baseplate 112, although mobile bearing configurations are also contemplated. Referring briefly to FIGS. 19 and 20, the mobile bearing features 286, 292 of the tibial articular insert 210 may be included in tibial articular insert 310 instead of the locking feature 386. The articular side 384 may include a first articular portion 388 for articulation against the articular side 116 of the femoral component 106. The first articular portion 388 may replicate the natural medial and lateral tibial articular condyles. The articular side 384 may also include a second articular portion 390, which in this example may be a hole that extends through the tibial articular insert 310 between the bone-facing side 382 and the articular side 384 along a superior-inferior direction. The second articular portion 390 may be referred to as a constraint feature. The second articular portion 390 in this example is for articulation with the shaft 328 of the post 316 of the adapter 308.

The tibial prosthesis 304 may be assembled by orienting the tibial baseplate 112 relative to the tibial articular insert 310 as shown in FIG. 22; and coupling the tibial baseplate 112 to the tibial articular insert 310. Coupling the tibial baseplate 112 to the tibial articular insert 310 may include engaging the locking features 386, 200 to fix the tibial baseplate 112 to the tibial articular insert 310. The holes 202, 390 may be aligned when the tibial prosthesis 304 is assembled.

When the tibial prosthesis 304 is assembled, the tibial articular insert 310 and the tibial baseplate 112 may be fixed together. The tibial articular insert 310 may be removably fixed to the tibial baseplate 112. A mobile bearing tibial articular insert is also contemplated, in which case the tibial articular insert 310 is free to move relative to the tibial baseplate 112 in use, at least within a limited range of motion.

Figure 21:
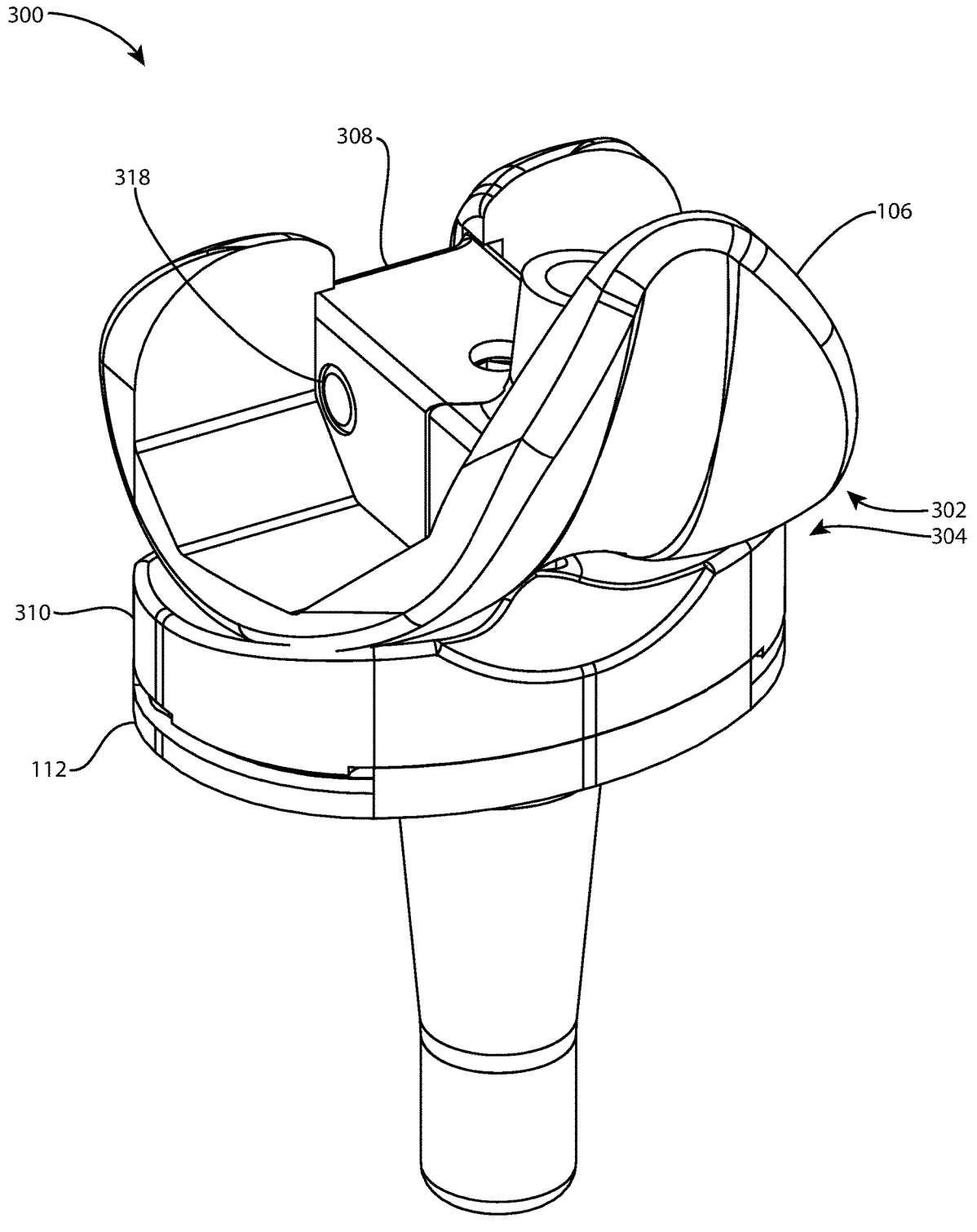
FIG. 21 is an oblique view of another knee arthroplasty system, in extension.

The knee arthroplasty system 300 may be assembled by orienting the femoral prosthesis 302 relative to the tibial prosthesis 304 as shown in FIG. 21; and bringing the femoral and tibial prostheses 302, 304 together so that the first articular portion 388 of the tibial articular insert 310 is against the articular side 116 of the femoral component 106 and the second articular portion 390 of the tibial articular insert 310 receives the shaft 328 of the post 316 of the adapter 308. Preferably, the post 316 is fixed to the sleeve 314 and inserted through the hole 390 into the hole 202 at this time. More specifically, with the knee in flexion, the distal end of the shaft 328 of the post 316 may be inserted from proximal to distal through the counterbore 322, the bore 320, and the hole 390, and into the hole 202; and the head 326 of the post 316 may be fixed in the counterbore 322 and/or bore 320.

Figures 31, 32, 33, 34:
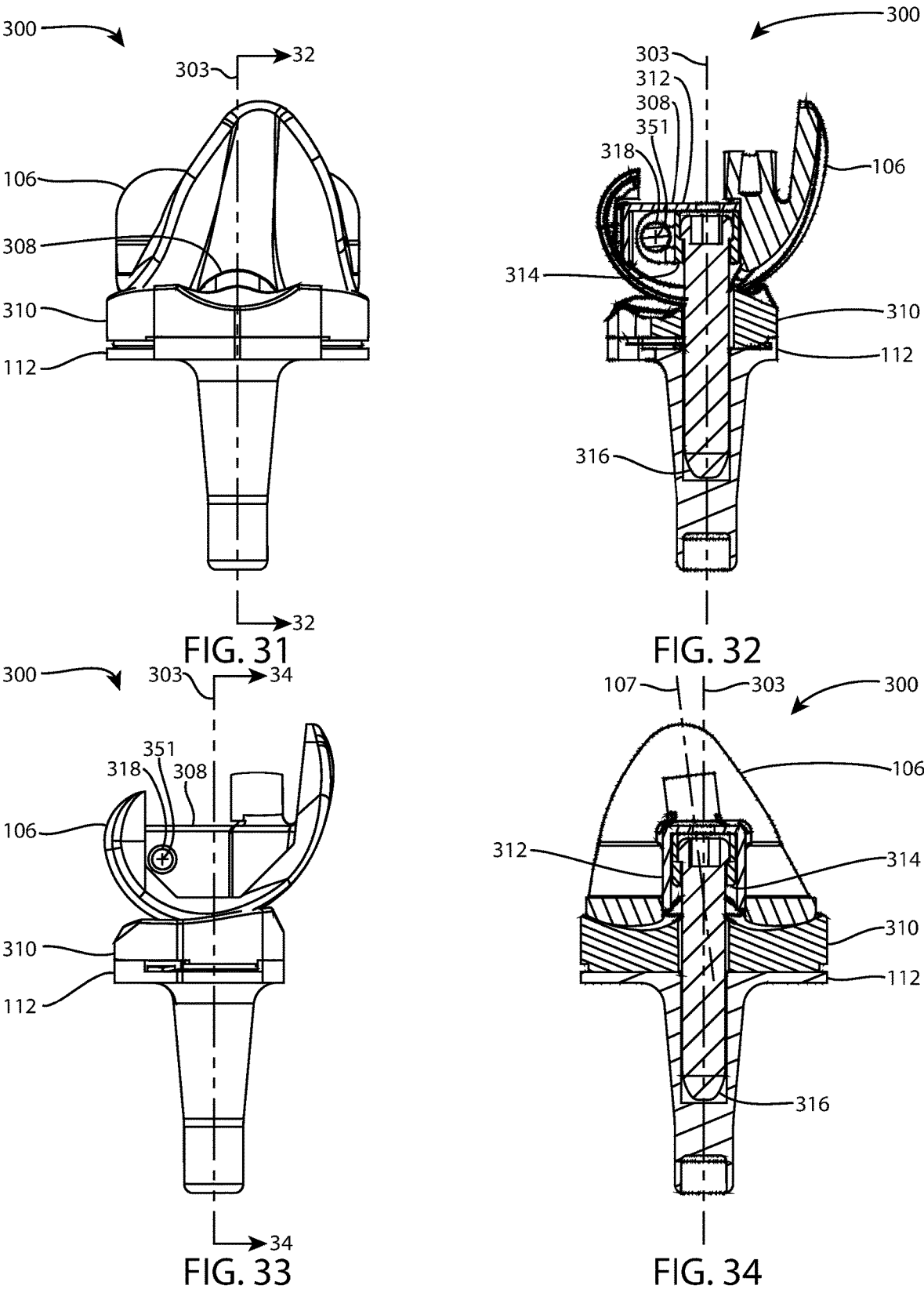
FIG. 31 is an anterior view of the knee arthroplasty system of FIG. 21, in extension.
FIG. 32 is a cross-sectional view of the knee arthroplasty system of FIG. 31, taken along section line 32-32 of FIG. 31.
FIG. 33 is a medial view of the knee arthroplasty system of FIG. 21, in extension.
FIG. 34 is a cross-sectional view of the knee arthroplasty system of FIG. 33, taken along section line 34-34 of FIG. 33.
Figure 35:
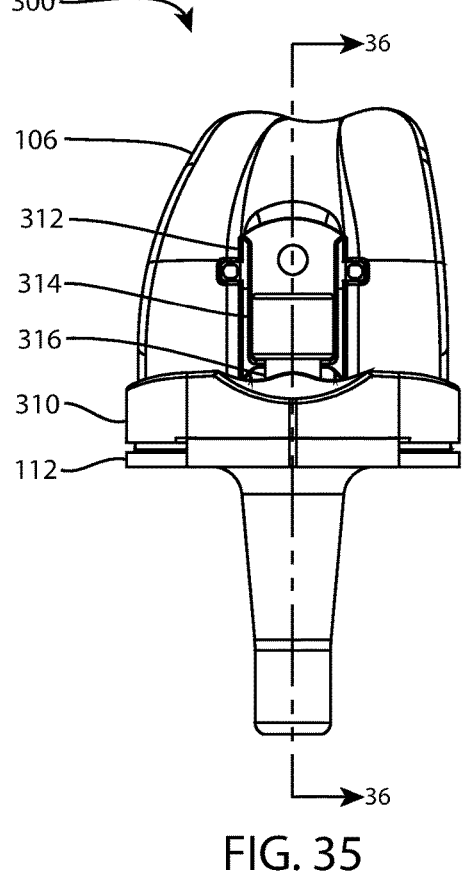
FIG. 35 is an anterior view of the knee arthroplasty system of FIG. 21, in flexion.
Figure 36:
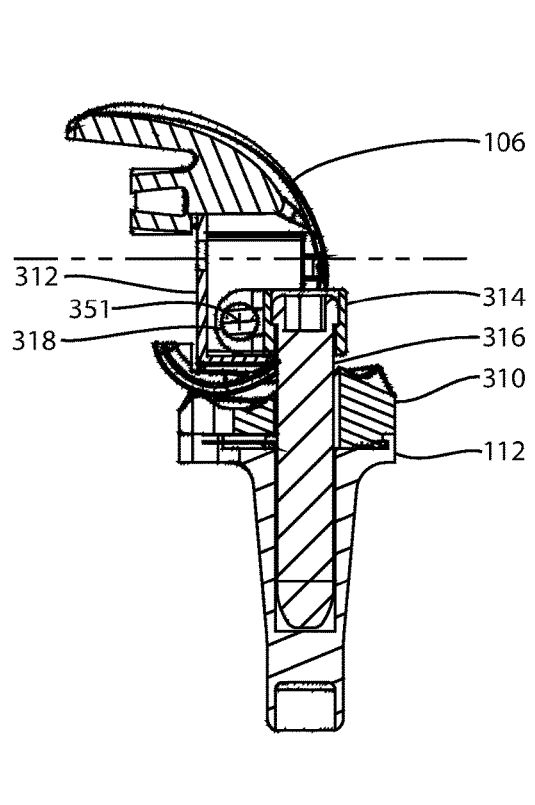
FIG. 36 is a cross-sectional view of the knee arthroplasty system of FIG. 35, taken along section line 36-36 of FIG. 35.

When the knee arthroplasty system 300 is assembled, the tibial prosthesis 304 articulates against the femoral prosthesis 302 to provide a range of motion between the tibial and femoral prostheses. The second articular portion 390 of the tibial articular insert 310 articulates with the shaft 328 of the adapter 308 to modify the nominal range of motion that would be possible if the second articular portion 390 and/or post 316 were absent. The knee arthroplasty system 300 has enhanced stability in use compared to a design that lacks the hinge constraint features of the second articular portion 390 and the post 316. More specifically, with reference to FIGS. 31-34, when the knee arthroplasty system 300 is in extension, the tibial prosthesis 304 has little to no translation relative to the femoral prosthesis 302 along directions that are perpendicular to the axis 303. Specifically, FIG. 32 shows that the tibial prosthesis 304 has little to no anterior-posterior translation and FIG. 34 shows that the tibial prosthesis has little to no medial-lateral translation. With reference to FIGS. 35 and 36, when the knee arthroplasty system 300 is in flexion, the tibial prosthesis 304 has little to no translation along a direction that is parallel to the axis 303. Specifically, FIG. 36 shows that the tibial prosthesis 304 has little to no superior translation. The tibial prosthesis 304 also has little to no medial-lateral translation in flexion.

With reference to FIGS. 35-38, the adapter 308 is insertable into, fixable within, and removable from the receptacle 124 along a direction that is parallel to the axis 303, from the distal articular side 116 toward the proximal bone-facing side 114, while the femoral prosthesis 302 is fixed to a distal femur. The adapter 308 is interchangeable with other distal adapters, such as adapter 108. Adapters can be exchanged before or after the femoral component 106 is fixed to the distal femur, even in a subsequent surgery.

A surgical method of implanting the knee arthroplasty system 300 may include some or all of the following steps in any order.

Preparing the distal femur may include making anterior, anterior chamfer, distal, posterior chamfer, and posterior resections to complement the bone-facing side 114 of the femoral component 106; drilling a hole to receive the socket 120, with or without a femoral intramedullary stem (not shown); and/or making a box cut to receive the pedestal 118 and/or adapter 308.

Fixing the femoral component 106 to the distal femur may include applying bone cement to the distal femur and/or the bone-facing side 114 of the femoral component 106, or press-fitting the femoral component 106 to the distal femur. Fasteners may be used to fix the femoral component to the distal femur.

Fixing the adapter 308 to the femoral component 106 may include flexing the knee; sliding the adapter body 312 into the receptacle 124 from distal to proximal; sliding the medial and lateral protrusions 370, 372 into the medial and lateral slots 148, 150; and fixing the adapter body to the femoral component. Fasteners may be used to fix the adapter to the femoral component. Preferably at this step, the adapter body 312 is coupled to at least the sleeve 314 and the pin 318.

Preparing the proximal tibia may include making a proximal tibial resection to complement the bone-facing side 192 of the tibial baseplate 112; and drilling a hole to receive the boss 196, with or without a tibial intramedullary stem (not shown).

Fixing the tibial baseplate 112 to the proximal tibia may include applying bone cement to the proximal tibia and/or the bone-facing side 192 of the tibial baseplate 112, or press-fitting the tibial baseplate 112 to the proximal tibia. Fasteners may be used to fix the tibial baseplate to the proximal tibia.

Coupling the tibial articular insert 310 to the tibial baseplate may include fixing the tibial articular insert to the tibial baseplate, or engaging mobile bearing features of the tibial articular insert and the tibial baseplate.

A surgical method of revising the knee arthroplasty system 300 may include some or all of the following steps in any order. Placing a previously-operated knee joint in flexion; exposing the adapter 308; releasing the post 316 from fixation to the sleeve 314; removing the post 316 from the holes 202, 390, bore 320, and counterbore 322; releasing the adapter body 312 from fixation to the femoral component 106; removing the adapter body from the receptacle along a proximal-to-distal direction; inserting a different adapter into the receptacle along a distal-to-proximal direction; fixing the different adapter to the femoral component 106; and closing the incision. The tibial articular insert 310 may be disconnected from the tibial baseplate 112 to facilitate access to the adapter 308, and optionally reconnected after the different adapter has been fixed to the femoral component. The tibial articular insert 310 may be replaced with a different tibial articular insert during the same revision surgical procedure, for example to convert between CCK and hinged or fixed and mobile designs.

Referring to FIGS. 39-50, yet another knee arthroplasty system 400 may include a femoral prosthesis 402 and/or the tibial prosthesis 104. This embodiment may be referred to as an anterior CCK fixed design. A left knee design is shown. The femoral prosthesis 402 may include a femoral component 406 and an adapter 408. The femoral prosthesis 402 may include additional components, such as a femoral intramedullary stem (not shown) or defect-filling augments (not shown). Referring to FIGS. 45-48, axis 403 corresponds to the femoral mechanical axis.

Figures 45, 46, 47, 48:
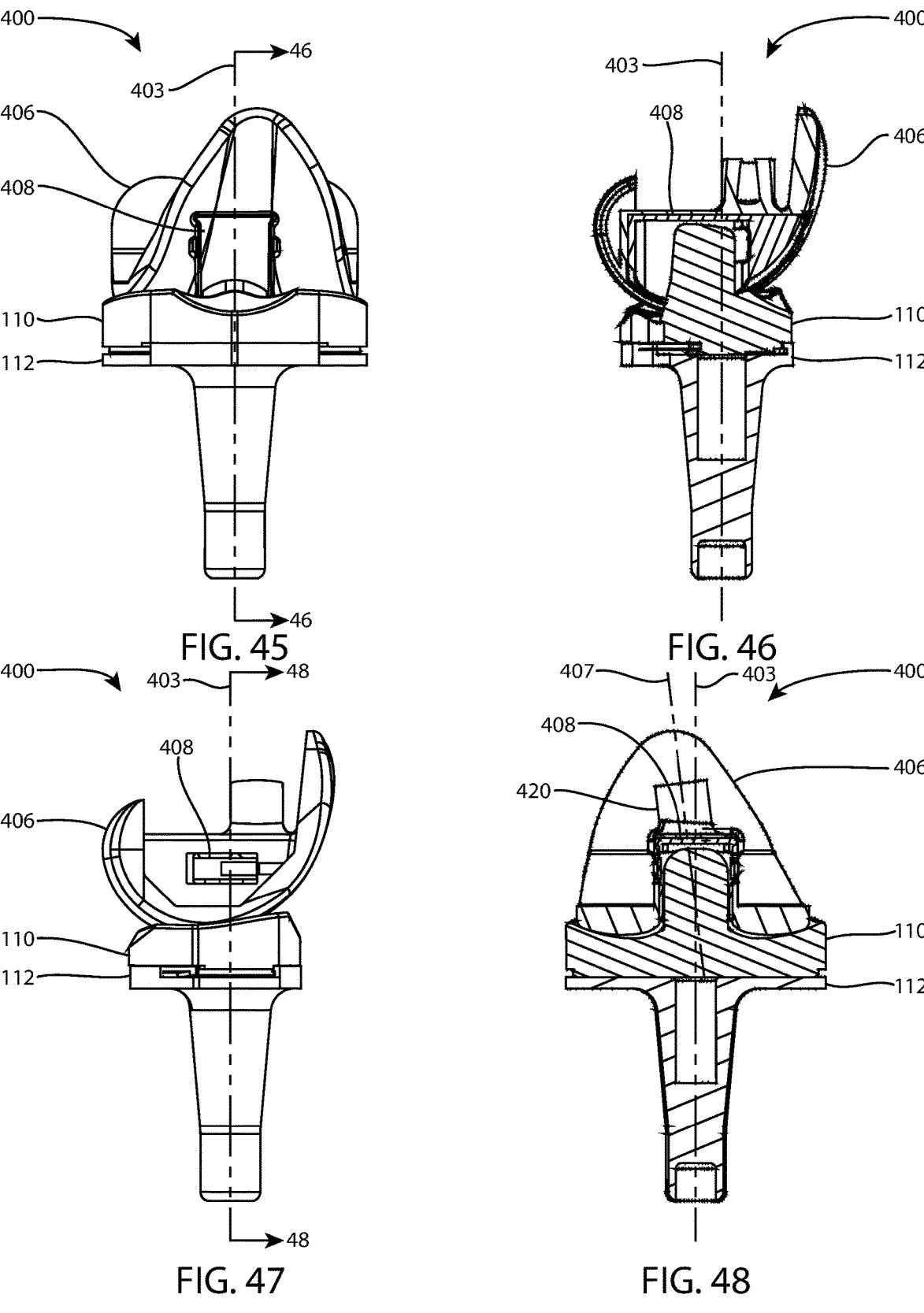
FIG. 45 is an anterior view of the knee arthroplasty system of FIG. 39, in extension.
FIG. 46 is a cross-sectional view of the knee arthroplasty system of FIG. 45, taken along section line 46-46 of FIG. 45.
FIG. 47 is a medial view of the knee arthroplasty system of FIG. 39, in extension.
FIG. 48 is a cross-sectional view of the knee arthroplasty system of FIG. 47, taken along section line 48-48 of FIG. 47.

The femoral component 406 includes a bone-facing side 414 and an opposite articular side 416. The bone-facing side 414 is configured to be fixed against a resected distal femur, for example by bone cement, press fit, or bone growth onto/into the bone-facing side. The bone-facing side 414 may include multiple portions corresponding to conventional anterior, anterior chamfer, distal, posterior chamfer, and/or posterior femoral resections. The bone-facing side 414 may include a pedestal 418 and/or a socket 420. The pedestal 418 in this example is a rectangular feature that protrudes superiorly from the surrounding bone-facing side. The pedestal 418 provides structural support for the socket 420, which protrudes superiorly from the superior aspect of the pedestal. The socket 420 may include a hole 422 to receive a femoral intramedullary stem (not shown). Referring to FIG. 48, the socket 420 and hole 422 are shown oriented along a generally superior-inferior axis 407 which may correspond to the femoral anatomical axis, also referred to as the femoral shaft axis. The articular side 416 is configured to articulate against a complementary articular side 184 of the tibial prosthesis 104, or against a natural articular surface of the proximal tibia. The articular side 416 may wrap around the anterior, distal, and posterior aspects of the femoral component 406 to replicate some or all of the natural articular surfaces of the distal femur.

Figures 49, 50:
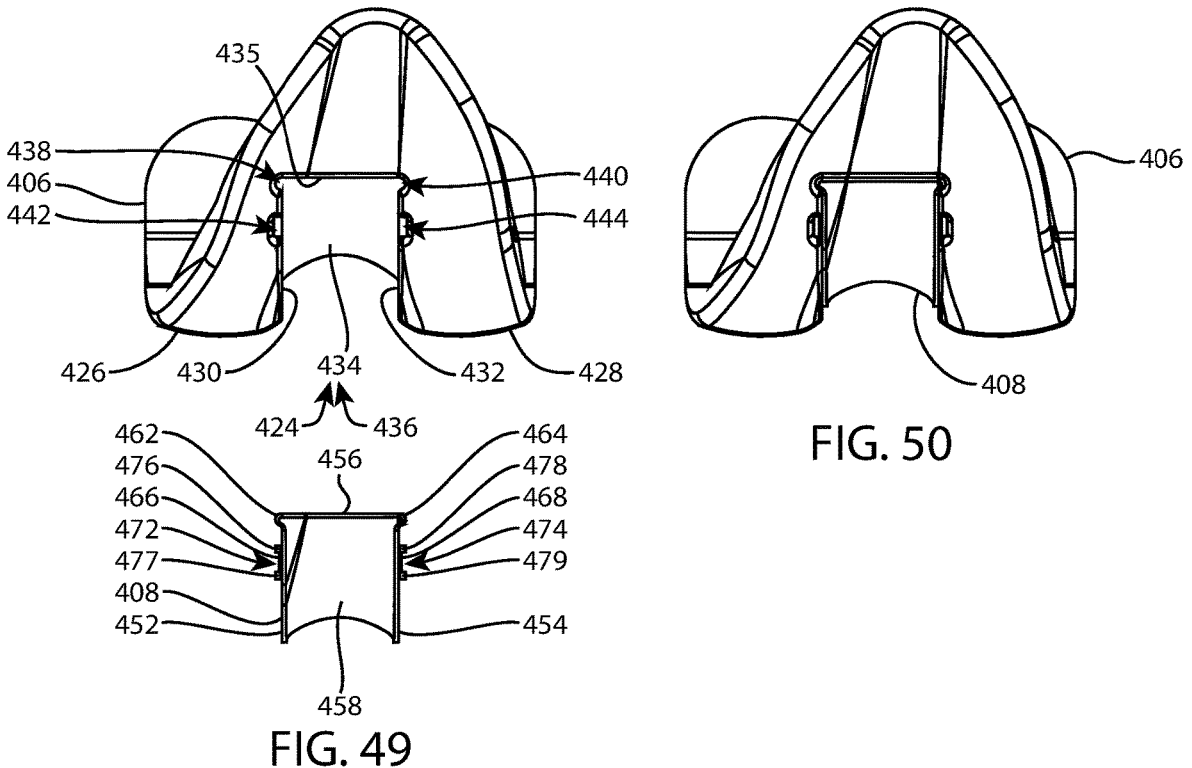
FIG. 49 is an anterior exploded view of the femoral component and adapter of the knee arthroplasty system of FIG. 45.
FIG. 50 is an anterior view of the assembled femoral component and adapter of the knee arthroplasty system of FIG. 45.

The femoral component 406 includes a receptacle 424, or space or alcove, which extends posteriorly into the anterior aspect of the femoral component between the medial and lateral condyles 426, 428. The receptacle 424 receives the adapter 408 or the adapter 508. Referring to FIG. 46, the receptacle 424 is shown extending along a direction that is perpendicular to the axis 403. Referring to FIG. 49, the receptacle 424 has a non-circular cross-sectional shape parallel to the axis 403 in the anterior view. A substantially rectangular cross-sectional shape is shown, although any shape that resists rotation may be used. More specifically, in this example, the receptacle 424 has planar medial and lateral walls 430, 432, planar posterior and superior walls 434, 435 and substantially open distal and anterior aspects 436, 437. Medial and lateral proximal grooves 438, 440 are shown extending perpendicular to the axis 403. Together, the medial and lateral proximal grooves 438, 440 form a proximal undercut channel; a distal undercut channel may also be present. Examples of undercut channels include dovetail channels, T-slots, and the like. The receptacle 424 may include a second pair of medial and lateral grooves 442, 444 which extend perpendicular to the axis 403, distal and parallel to the medial and lateral proximal grooves 438, 440. A window 446 may extend through the medial and lateral walls 430, 432 and intersect the posterior ends of the grooves 442, 444. The receptacle 424 may include one or more insertion stop features which prevent over-insertion of the adapter 408 or 508 into the receptacle. In this example, the posterior wall 434 may function as an insertion stop. The receptacle 424 may include one or more removal stop features which prevent unintentional removal of the adapter from the receptacle. The anterior walls of the window 446 on either side of the grooves 442, 444 may function as removal stops. Medial proximal and distal removal stops 448, 449 and lateral distal removal stop 450 are visible in FIGS. 41-42; a lateral proximal removal stop is hidden from view in FIG. 41.

The adapter 408 is received in the receptacle 424 of the femoral component 406 along a direction from the articular side 416 toward the bone-facing side 414. This means that the adapter 408 may be inserted into, fixed within, and removed from the receptacle 424 while the femoral component 406 is fixed to the distal femur, during the initial surgical procedure or during a subsequent surgical procedure. In this example, the adapter 408 is inserted along an anterior-to-posterior direction perpendicular to the axis 403. However, the adapter 408 may be inserted along other directions, such as distal-to-proximal parallel to the axis 403 as discussed above, or along oblique directions, such as distal-anterior to proximal-posterior at a 45 degree angle to the axis 403. The adapter insertion direction may be based upon the particular characteristics of the joint and arthroplasty prosthesis.

Figures 43, 44:
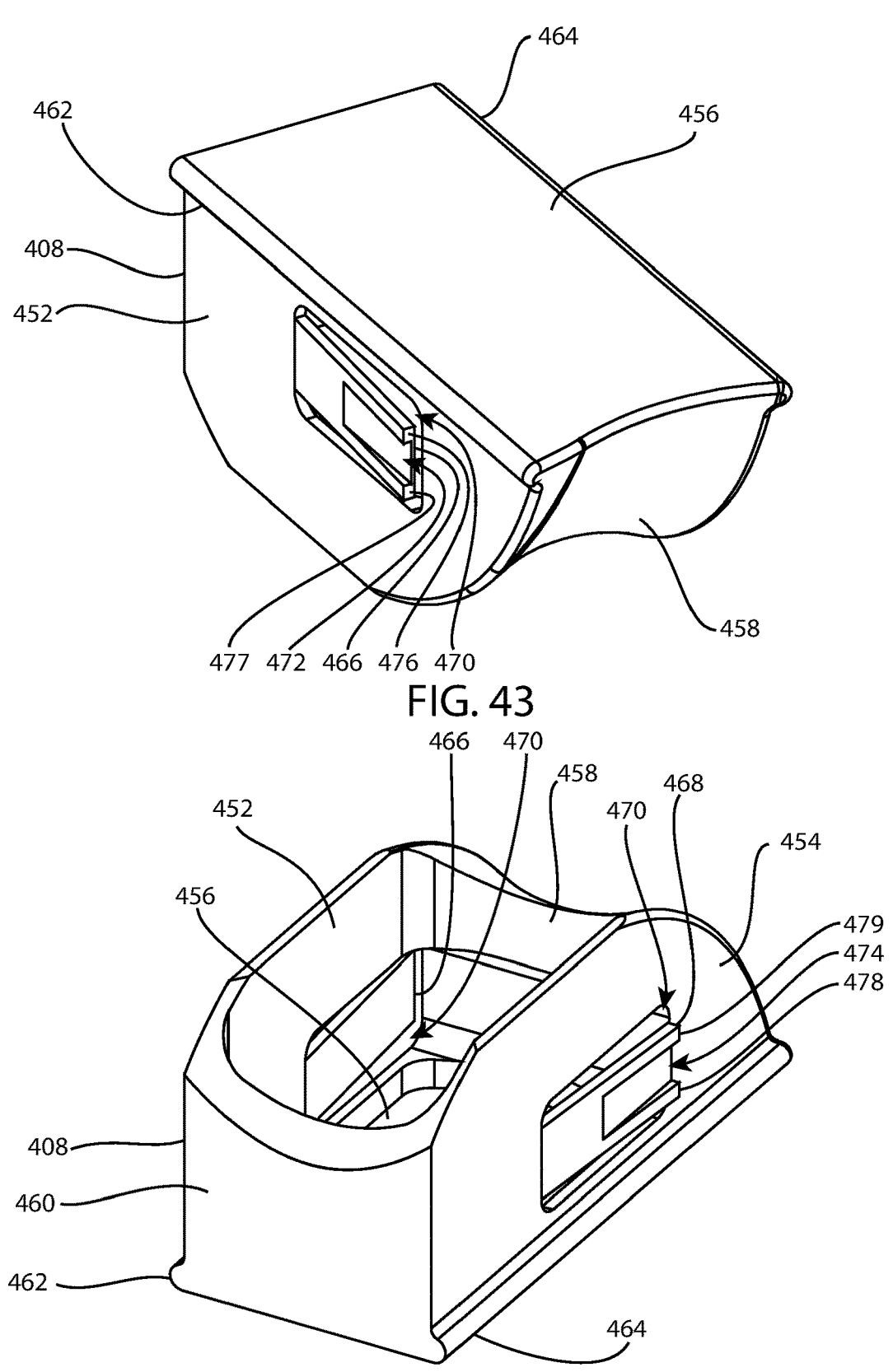
FIG. 43 is an oblique view of an adapter of the knee arthroplasty system of FIG. 39.
FIG. 44 is another oblique view of the adapter of FIG. 43, from a different direction.

The adapter 408 has an exterior shape which is complementary to the shape of the receptacle 424. Referring to FIG. 49, the adapter 408 has a non-circular exterior cross-sectional shape parallel to the axis 403 in the anterior view. A substantially rectangular cross-sectional shape is shown, although any shape that resists rotation may be used. More specifically, in this example, the adapter 408 has planar medial and lateral walls 452, 454, a planar superior wall 456, and a planar posterior wall 460. Referring to FIGS. 43, 44, and 46, an anterior wall 458 may be present; its exterior anterior aspect may blend with the trochlear groove of the articular side 416 of the femoral component 406. The distal aspect is open. Medial and lateral proximal ridges 462, 464 are shown extending perpendicular to the axis 403. Together, the medial and lateral proximal ridges 462, 464 form a proximal undercut rail; a distal undercut rail may also be present. Examples of undercut rails include dovetail rails, T-rails, and the like. The medial and lateral walls 452, 454 may include medial and lateral arms 466, 468, respectively. The posterior ends of the arms 466, 468 may be integrally formed with the walls 452, 454, while the proximal, anterior, and distal sides of the arms 466, 468 may be separated from the walls 452, 454 by a U-shaped slit 470, or window, that extends through the medial and lateral walls 452, 454. Each arm 466, 468 may angle outwardly from posterior to anterior, so that the anterior free ends of the arms 466, 468 protrude outwardly from the walls 452, 454. The medial and lateral arms 466, 468 may include medial and lateral exterior grooves 472, 474 which may be deepest at the anterior ends of the arms, becoming shallower toward the posterior ends of the arms. The adapter 408 may include one or more insertion stop features which prevent over-insertion of the adapter into the receptacle 424. The posterior wall 460 may function as an insertion stop against the posterior wall 434 of the femoral component 406. The adapter 408 may include one or more removal stop features which prevent unintentional removal of the adapter from the receptacle 424. The anterior ends of the arms 466, 468 on either side of the grooves 472, 474 may function as removal stops. Medial proximal and distal removal stops 476, 477 are shown in FIG. 43 and lateral proximal and distal removal stops 478, 479 are shown in FIG. 44. The walls 452, 454, 456, 458, 460 define an interior cavity 480 or space, which may be substantially rectangular. The cavity 480 may be referred to as a constraint feature. The cavity 480 may include a cam for interaction with the second articular portion 190 of the tibial articular insert 110, described above.

Figure 40:
FIG. 40 is an oblique exploded view of the knee arthroplasty system of FIG. 39.
Figure 40:
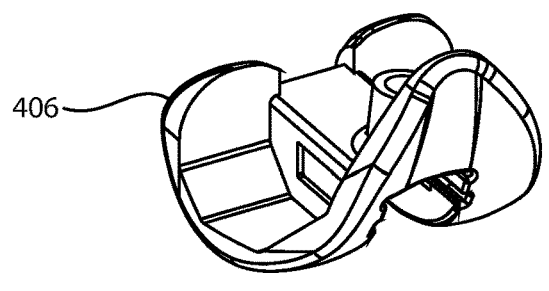
Figure 40:
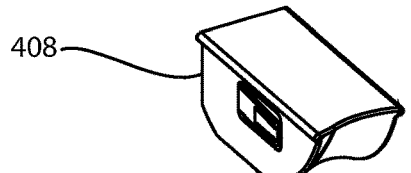
Figure 40:
Figure 40:
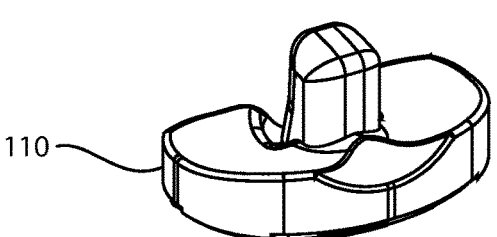
Figure 40:
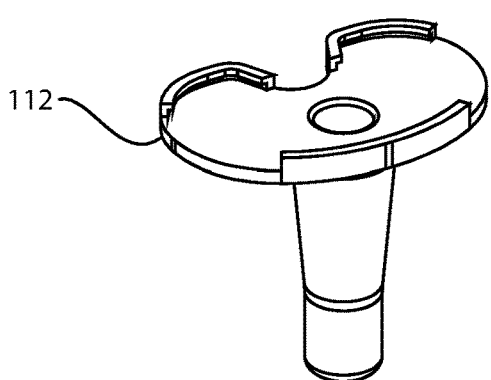
Figure 41:
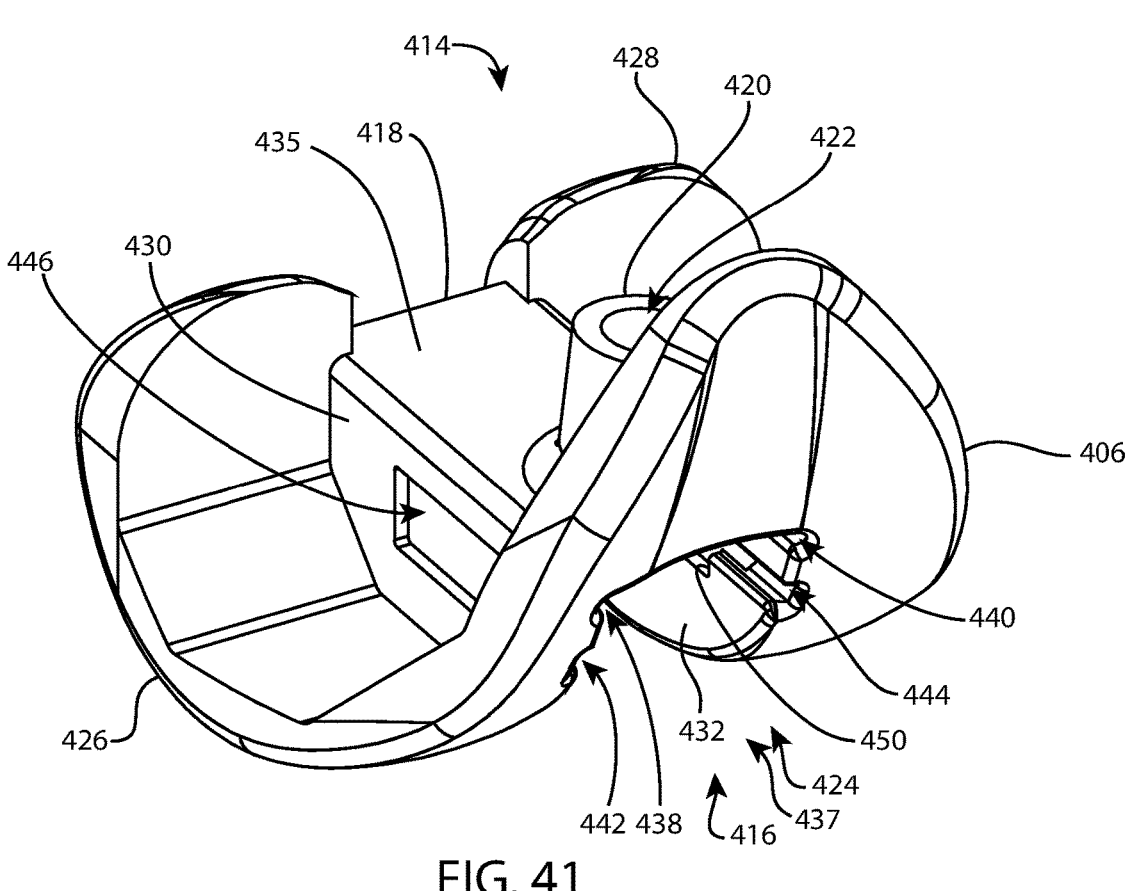
FIG. 41 is an oblique view of a femoral component of the knee arthroplasty system of FIG. 39.
Figure 42:
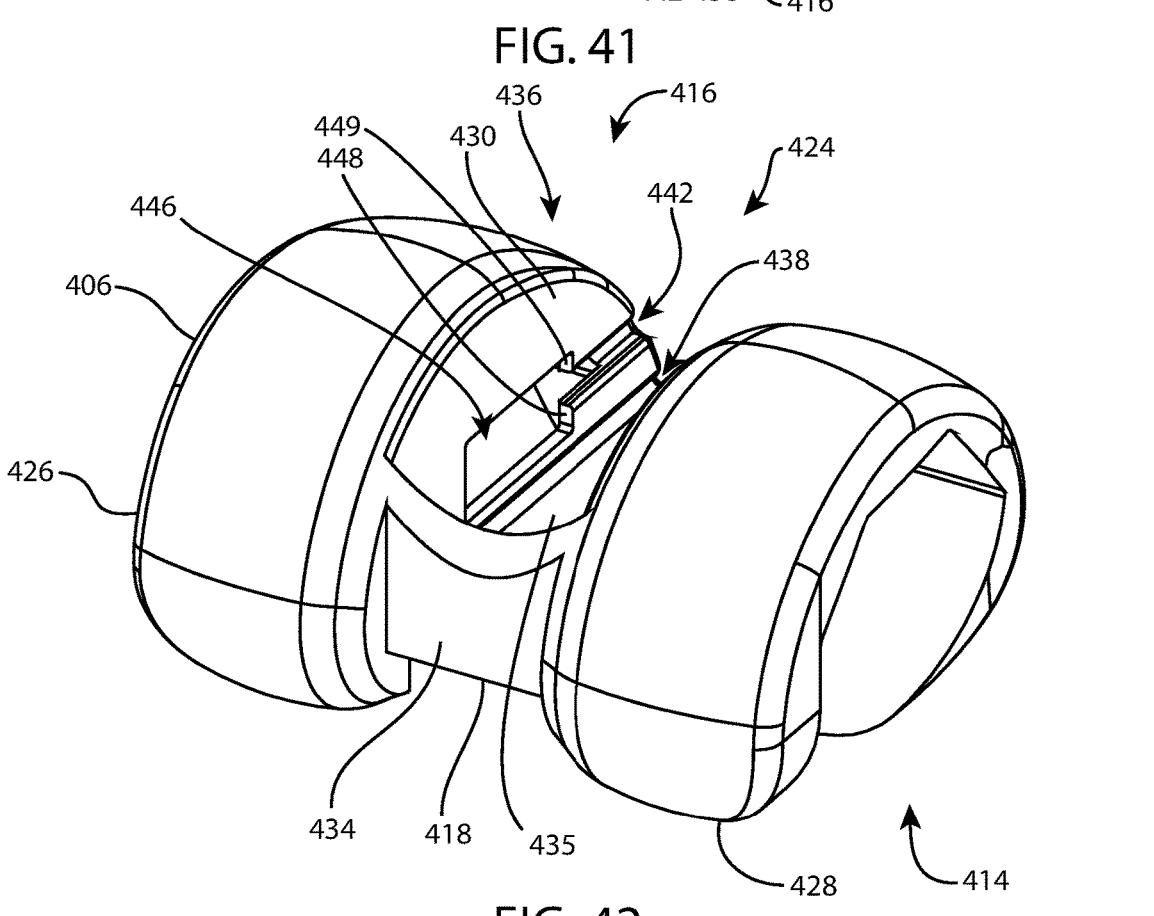
FIG. 42 is another oblique view of the femoral component of FIG. 41, from a different direction.

The femoral prosthesis 402 may be assembled by orienting the adapter 408 relative to the femoral component 406 as shown in FIG. 40; sliding the adapter into the receptacle 424 until at least one adapter insertion stop feature contacts a femoral component insertion stop feature; and fixing the adapter to the femoral component. The adapter 408 may slide into the receptacle 424 along a direction from the articular side 416 toward the bone-facing side 414, which in this example is from anterior to posterior. The arms 466, 468 may be elastically deformed inwardly as the adapter 408 enters the receptacle 424, and may spring outwardly to occupy the window 446 as the adapter is fully seated in the receptacle. The adapter 408 may be fixed to the femoral component 406 by the arms 466, 468 in the window 446. More specifically, the medial proximal removal stop features 448, 476; the medial distal removal stop features 449, 477; the lateral proximal removal stop features (femoral hidden), 478; and/or the lateral distal removal stop features 450, 479 may become engaged to fix the adapter to the femoral component. The removal stop features may be disengaged by inserting a tool into the grooves 442, 472 and/or 444, 474 to press the arms 466, 468 inwardly. For example, the tool may resemble a tuning fork with a pair of protruding prongs.

When the femoral prosthesis 402 is assembled, the femoral component 406 and the adapter 408 are fixed together. The adapter 408 is insertable into, fixable within, and removable from the receptacle 424 when the femoral prosthesis 402 is fixed to a distal femur. The adapter 408 is interchangeable with other anterior adapters, such as adapter 508 discussed below.

Figure 39:
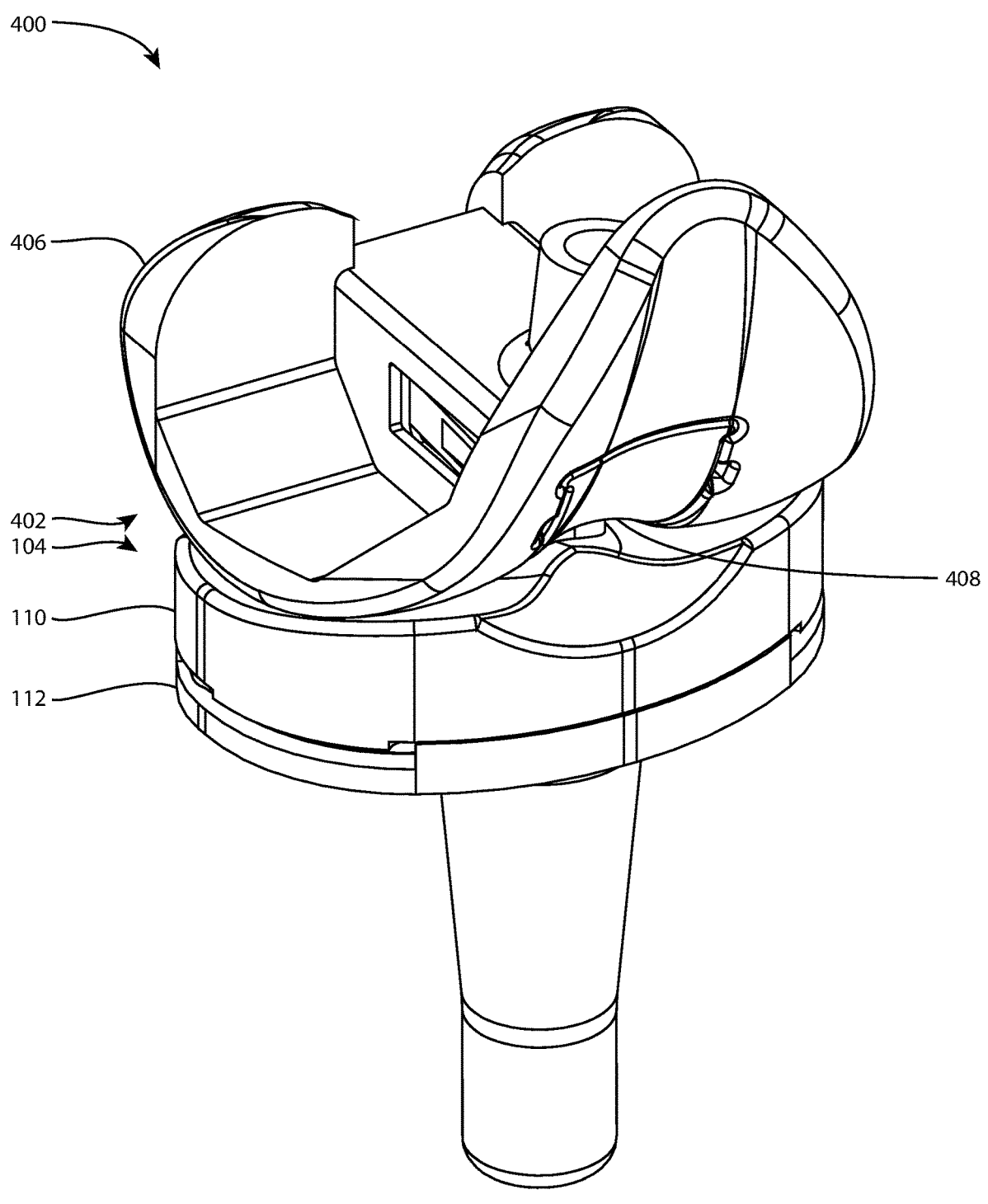
FIG. 39 is an oblique view of yet another knee arthroplasty system, in extension.

The knee arthroplasty system 400 may be assembled by orienting the femoral prosthesis 402 relative to the tibial prosthesis 104 as shown in FIG. 39; and bringing the femoral and tibial prostheses 402, 104 together so that the first articular portion 188 of the tibial articular insert 110 is against the articular side 416 of the femoral component 406 and the second articular portion 190 of the tibial articular insert 110 is received in the cavity 480 of the adapter 408.

When the knee arthroplasty system 400 is assembled, the tibial prosthesis 104 articulates against the femoral prosthesis 402 to provide a range of motion between the tibial and femoral prostheses. The second articular portion 190 of the tibial articular insert 110 articulates within the cavity 480 of the adapter 408 to modify the nominal range of motion that would be possible if the second articular portion 190 was absent. The knee arthroplasty system 400 has enhanced stability in use compared to a design that lacks the CCK constraint features of the second articular portion 190 and the cavity 480. More specifically, with reference to FIGS. 45-48, when the knee arthroplasty system 400 is in extension, the tibial prosthesis 104 has limited translation relative to the femoral prosthesis 402 along directions that are perpendicular to the axis 403. Specifically, FIG. 46 shows that the tibial prosthesis 104 has limited anterior-posterior translation and FIG. 48 shows that the tibial prosthesis has limited medial-lateral translation. As shown in FIGS. 15 and 16 for knee arthroplasty system 100, when the knee arthroplasty system 400 is in flexion, the tibial prosthesis 104 has limited translation along a direction that is parallel to the axis 403. Specifically, FIG. 16 shows that the tibial prosthesis 104 has limited superior translation. The tibial prosthesis 104 also has limited medial-lateral translation in flexion.

With reference to FIGS. 49-50, the adapter 408 is insertable into, fixable within, and removable from the receptacle 424 along an anterior-posterior direction that is perpendicular to the axis 403, from the anterior articular side 416 toward the posterior bone-facing side 414, while the femoral prosthesis 402 is fixed to a distal femur. The adapter 408 is interchangeable with other anterior adapters, such as adapter 508. Adapters can be exchanged before or after the femoral component 406 is fixed to the distal femur, even in a subsequent surgery.

A surgical method of implanting the knee arthroplasty system 400 may include some or all of the following steps in any order.

Preparing the distal femur may include making anterior, anterior chamfer, distal, posterior chamfer, and posterior resections to complement the bone-facing side 414 of the femoral component 406; drilling a hole to receive the socket 420, with or without a femoral intramedullary stem (not shown); and/or making a box cut to receive the pedestal 418 and/or adapter 408.

Fixing the femoral component 406 to the distal femur may include applying bone cement to the distal femur and/or the bone-facing side 414 of the femoral component 406, or press-fitting the femoral component 406 to the distal femur. Fasteners may be used to fix the femoral component to the distal femur.

Fixing the adapter 408 to the femoral component 406 may include extending or flexing the knee; sliding the adapter into the receptacle 424 from anterior to posterior; sliding the medial and lateral arms 466, 468 into the window 446; and fixing the adapter to the femoral component. Optional fasteners may be used to fix the adapter to the femoral component.

Preparing the proximal tibia may include making a proximal tibial resection to complement the bone-facing side 192 of the tibial baseplate 112; and drilling a hole to receive the boss 196, with or without a tibial intramedullary stem (not shown).

Fixing the tibial baseplate 112 to the proximal tibia may include applying bone cement to the proximal tibia and/or the bone-facing side 192 of the tibial baseplate 112, or press-fitting the tibial baseplate 112 to the proximal tibia. Fasteners may be used to fix the tibial baseplate to the proximal tibia.

Coupling the tibial articular insert 110 to the tibial baseplate may include fixing the tibial articular insert to the tibial baseplate, or engaging mobile bearing features of the tibial articular insert and the tibial baseplate.

A surgical method of revising the knee arthroplasty system 400 may include some or all of the following steps in any order. Placing a previously-operated knee joint in extension or flexion; exposing the adapter 408; releasing the adapter from fixation to the femoral component 406; removing the adapter from the receptacle along a posterior-to-anterior direction; inserting a different adapter into the receptacle along an anterior-to-posterior direction; fixing the different adapter to the femoral component 406; and closing the incision. The tibial articular insert 110 may be disconnected from the tibial baseplate 112 to facilitate access to the adapter 408, and optionally reconnected after the different adapter has been fixed to the femoral component. The tibial articular insert 110 may be replaced with a different tibial articular insert during the same revision surgical procedure, for example to convert between CCK and hinged or fixed and mobile designs.

Referring to FIGS. 51-60, yet another knee arthroplasty system 500 may include a femoral prosthesis 502 and/or the tibial prosthesis 304. This embodiment may be referred to as an anterior hinged fixed design. A left knee design is shown. The femoral prosthesis 502 may include the femoral component 406 and an adapter 508. The adapter 508 may be a sub-assembly of multiple parts. The femoral prosthesis 502 may include additional components, such as a femoral intramedullary stem (not shown) or defect-filling augments (not shown). Referring to FIGS. 55-58, axis 503 corresponds to the femoral mechanical axis.

Figure 52:
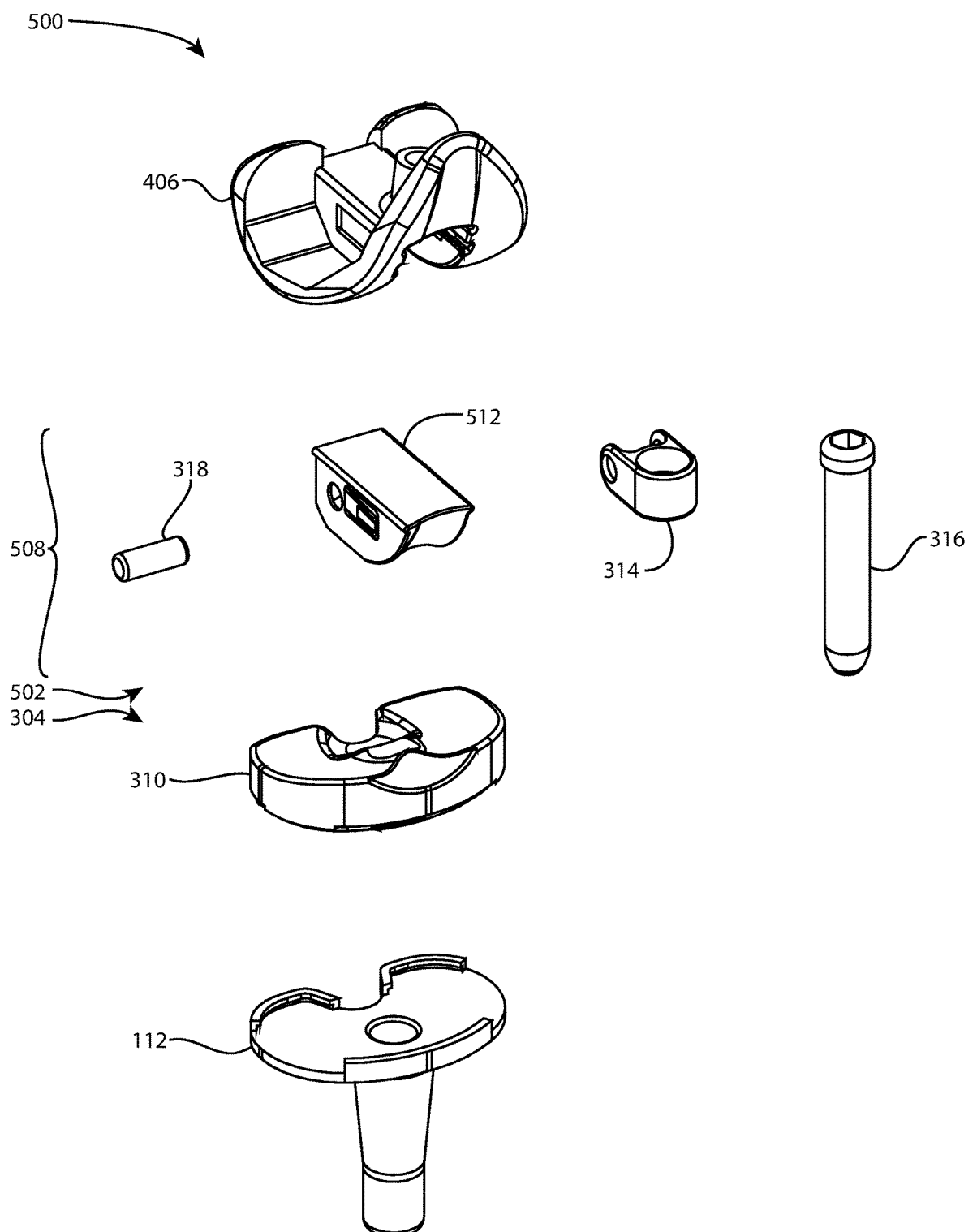
FIG. 52 is an oblique exploded view of the knee arthroplasty system of FIG. 51.

Referring to FIG. 52, the adapter 508 may include an adapter body 512, the sleeve 314, the post 316, and the pin 318. The adapter 508 is received in the receptacle 424 of the femoral component 406 along a direction from the articular side 416 toward the bone-facing side 414. This means that the adapter 508 may be inserted into, fixed within, and removed from the receptacle 424 while the femoral component 406 is fixed to the distal femur, during the initial surgical procedure or during a subsequent surgical procedure. In this example, the adapter 508 is inserted along an anterior-to-posterior direction perpendicular to the axis 503. However, the adapter 508 may be inserted along other directions, such as distal-to-proximal parallel to the axis 503 as discussed above, or along oblique directions, such as distal-anterior to proximal-posterior at a 45 degree angle to the axis 503. The adapter insertion direction may be based upon the particular characteristics of the joint and arthroplasty prosthesis.

Figures 53, 54:
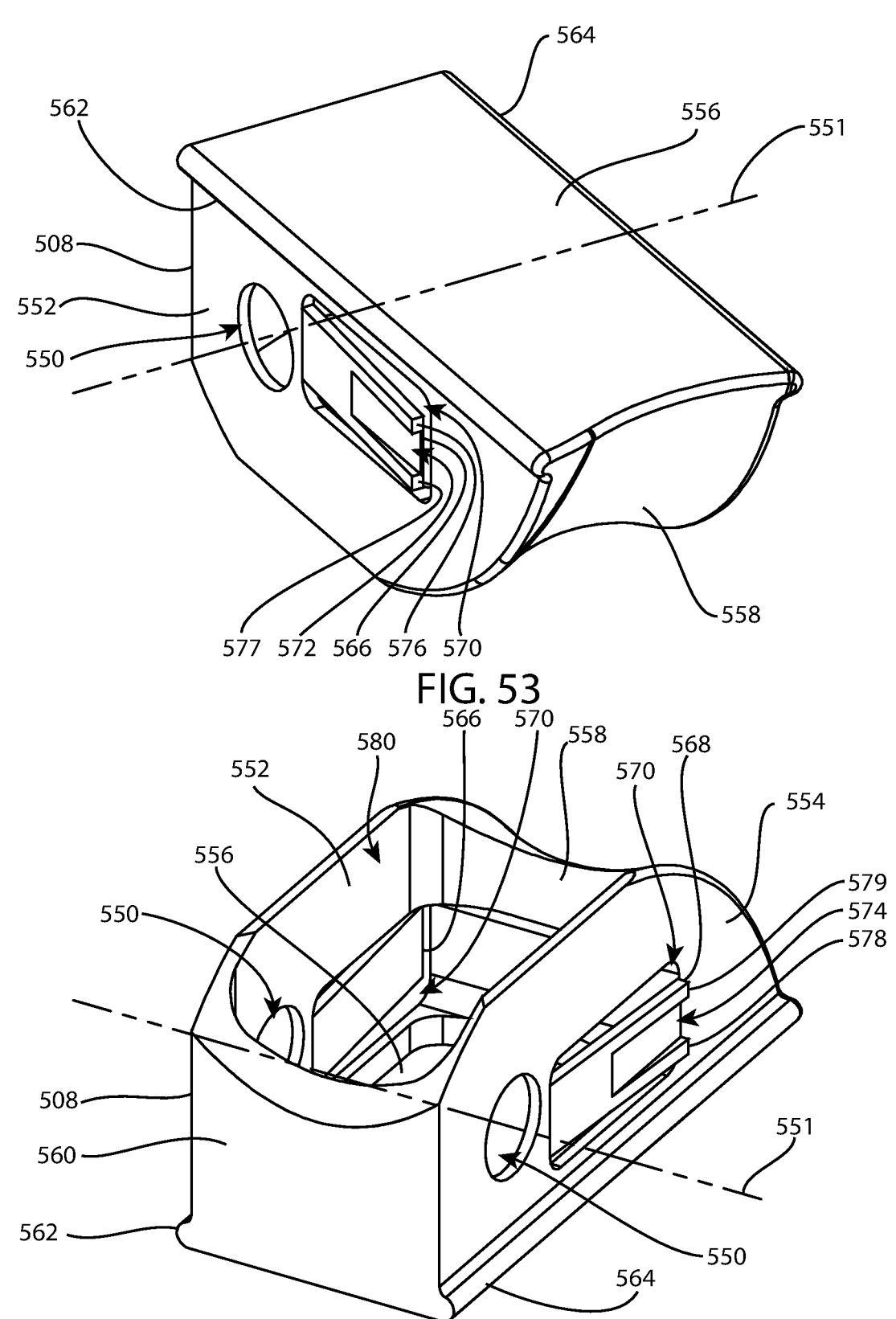
FIG. 53 is an oblique view of an adapter of the knee arthroplasty system of FIG. 51.
FIG. 54 is another oblique view of the adapter of FIG. 53, from a different direction.
Figures 59, 60:
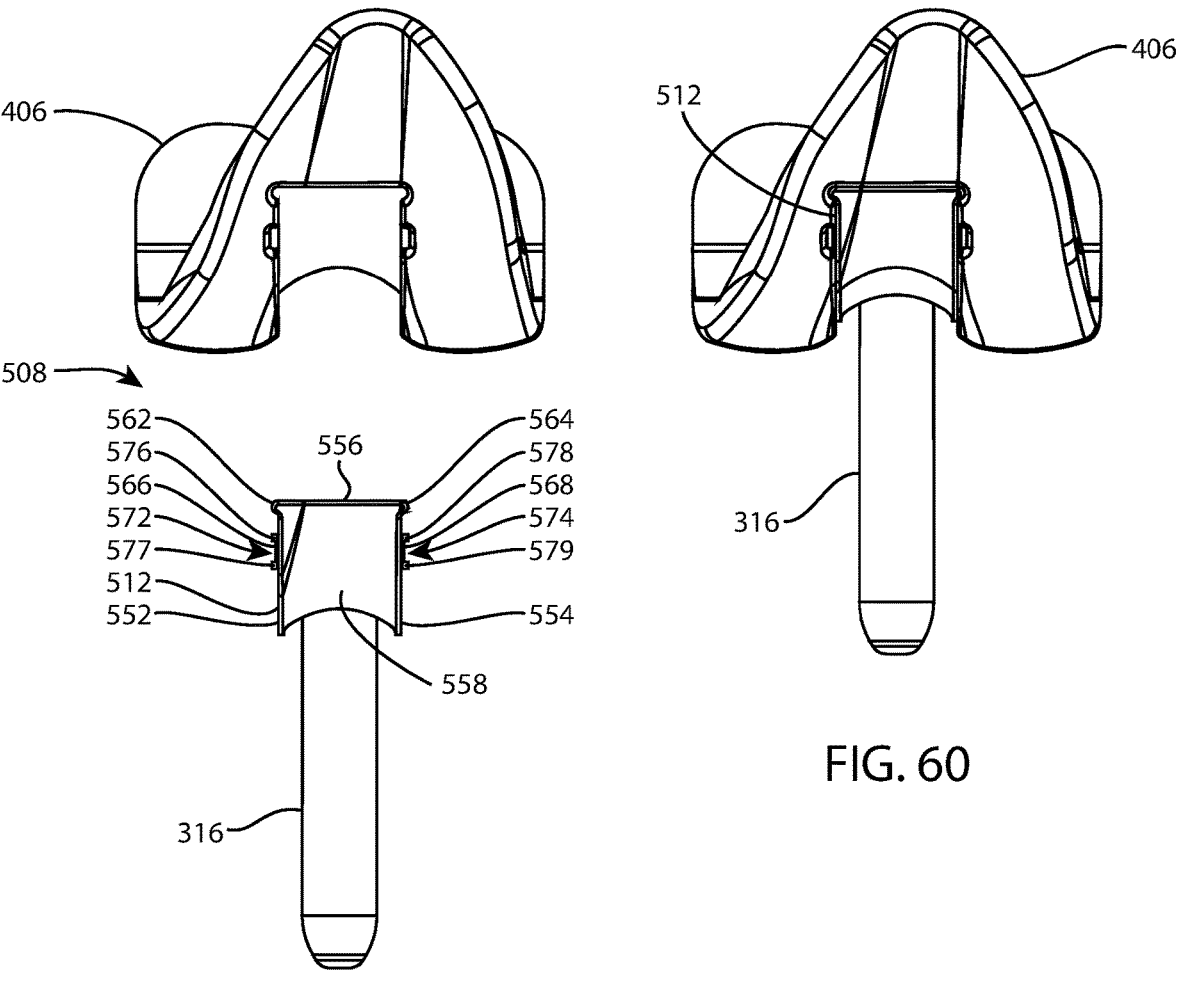
FIG. 59 is an anterior exploded view of the femoral component and adapter of the knee arthroplasty system of FIG. 55.
FIG. 60 is an anterior view of the assembled femoral component and adapter of the knee arthroplasty system of FIG. 55.

The adapter body 512 has an exterior shape which is complementary to the shape of the receptacle 424. Referring to FIG. 59, the adapter body 512 has a non-circular exterior cross-sectional shape parallel to the axis 503 in the anterior view. A substantially rectangular cross-sectional shape is shown, although any shape that resists rotation may be used. More specifically, in this example, the adapter 508 has planar medial and lateral walls 552, 554, a planar superior wall 556, and a planar posterior wall 560. Referring to FIGS. 53-56, an anterior wall 558 may be present; its exterior anterior aspect may blend with the trochlear groove of the articular side 416 of the femoral component 406. The distal aspect is open. Medial and lateral proximal ridges 562, 564 are shown extending perpendicular to the axis 503. Together, the medial and lateral proximal ridges 562, 564 form a proximal undercut rail; a distal undercut rail may also be present. Examples of undercut rails include dovetail rails, T-rails, and the like. The medial and lateral walls 552, 554 may include medial and lateral arms 566, 568, respectively. The posterior ends of the arms 566, 568 may be integrally formed with the walls 552, 554, while the proximal, anterior, and distal sides of the arms 566, 568 may be separated from the walls 552, 554 by a U-shaped slit 570, or window, that extends through the medial and lateral walls 552, 554. Each arm 566, 568 may angle outwardly from posterior to anterior, so that the anterior free ends of the arms 566, 568 protrude outwardly from the walls 552, 554. The medial and lateral arms 566, 568 may include medial and lateral exterior grooves 572, 574 which may be deepest at the anterior ends of the arms, becoming shallower toward the posterior ends of the arms. The adapter 508 may include one or more insertion stop features which prevent over-insertion of the adapter into the receptacle 424. The posterior wall 560 may function as an insertion stop against the posterior wall 434 of the femoral component 406. The adapter 508 may include one or more removal stop features which prevent unintentional removal of the adapter from the receptacle 424. The anterior ends of the arms 566, 568 on either side of the grooves 572, 574 may function as removal stops. Medial proximal and distal removal stops 576, 577 are shown in FIG. 53 and lateral proximal and distal removal stops 578, 579 are shown in FIG. 54. The walls 552, 554, 556, 568, 560 define an interior cavity 580 or space, which may be substantially rectangular. The cavity 580 may be referred to as a constraint feature. A hole 550 may extend through the adapter body 512 along a medial-lateral direction to establish a hinge axis 551 which is perpendicular to the axis 503. The hole 550 receives the pin 318.

The adapter 508 may be assembled by orienting the sleeve 314 relative to the adapter body 512 as shown in FIG. 52; inserting the sleeve into the cavity 580 so that the holes 550, 324 are aligned; inserting the pin 318 through the holes 550, 324 so that the sleeve 314 is free to rotate relative to the adapter body 512 about the hinge axis 551; orienting the post 316 relative to the sleeve 314 as shown in FIG. 52; and fixing the head 326 of the post 316 in the bore 320 and/or counterbore 322 of the sleeve 314 so that the shaft 328 of the post 316 protrudes distally from the bore 320. The adapter 508 may be provided in a partially assembled state with the adapter body 512, the sleeve 314, and the pin 318 coupled together, with the step of fixing the head 326 of the post 316 in the bore 320 and/or counterbore 322 of the sleeve 314 performed during the surgical procedure.

When the adapter 508 is assembled, the fixed-together sleeve 314 and post 316 are free to rotate relative to the adapter body 512 about the hinge axis 551.

The femoral prosthesis 502 may be assembled by orienting the adapter body 512 relative to the femoral component 406 as shown in FIG. 52, the adapter body 512 preferably coupled to at least the sleeve 314 and the pin 318; sliding the adapter body into the receptacle 424 until at least one adapter insertion stop feature contacts a femoral component insertion stop feature; fixing the adapter body to the femoral component; orienting the post 316 relative to the sleeve 314 as shown in FIG. 52; and fixing the head 326 of the post 316 in the bore 320 and/or counterbore 322 of the sleeve 314 so that the shaft 328 of the post 316 protrudes distally from the bore 320. The adapter body 512 may slide into the receptacle 424 along a direction from the articular side 416 toward the bone-facing side 414, which in this example is from anterior to posterior. The arms 566, 568 may be elastically deformed inwardly as the adapter 508 enters the receptacle 424, and may spring outwardly to occupy the window 446 as the adapter is fully seated in the receptacle. The adapter 508 may be fixed to the femoral component 406 by the arms 566, 568 in the window 446. More specifically, the medial proximal removal stop features 448, 576; the medial distal removal stop features 449, 577; the lateral proximal removal stop features (femoral hidden), 578; and/or the lateral distal removal stop features 450, 579 may become engaged to fix the adapter to the femoral component. The removal stop features may be disengaged by inserting a tool into the grooves 442, 572 and/or 444, 574 to press the arms 566, 568 inwardly. For example, the tool may resemble a tuning fork with a pair of protruding prongs.

When the femoral prosthesis 502 is assembled, the femoral component 406 and the adapter body 512 are fixed together, and the sleeve 314 and post 316 (if attached) are free to rotate relative to the adapter body 512 about the hinge axis 551. The adapter body 512 is insertable into, fixable within, and removable from the receptacle 424 when the femoral prosthesis 502 is fixed to a distal femur. The adapter 508 is interchangeable with other anterior adapters, such as adapter 408.

Figure 51:
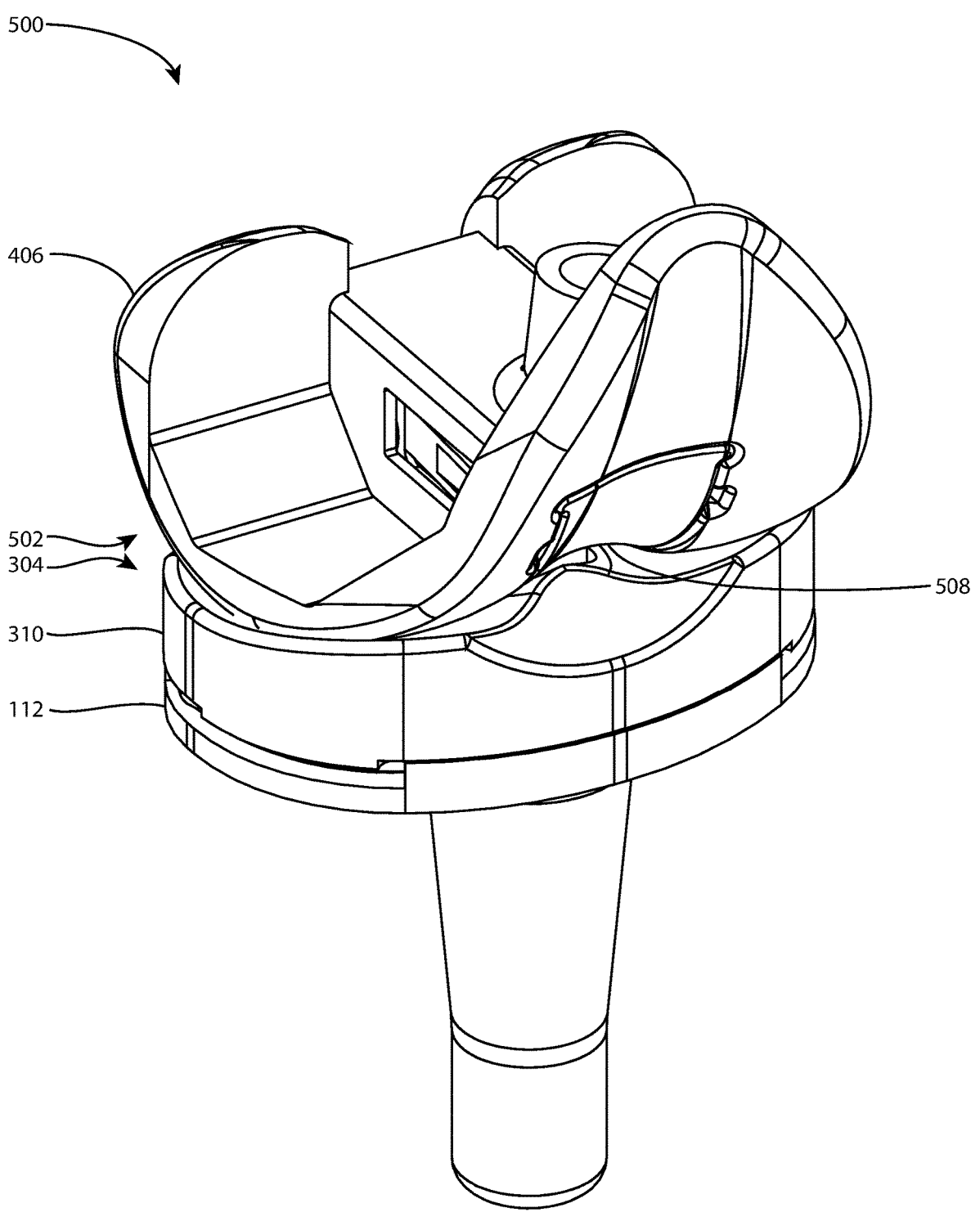
FIG. 51 is an oblique view of yet another knee arthroplasty system, in extension.

The knee arthroplasty system 500 may be assembled by orienting the femoral prosthesis 502 relative to the tibial prosthesis 304 as shown in FIG. 51; and bringing the femoral and tibial prostheses 502, 304 together so that the first articular portion 388 of the tibial articular insert 310 is against the articular side 416 of the femoral component 406 and the second articular portion 390 of the tibial articular insert 310 receives the shaft 328 of the post 316 of the adapter 508. Preferably, the post 316 is fixed to the sleeve 314 and inserted through the hole 390 into the hole 202 at this time. More specifically, with the knee in flexion, the distal end of the shaft 328 of the post 316 may be inserted from proximal to distal through the counterbore 322, the bore 320, and the hole 390, and into the hole 202; and the head 326 of the post 316 may be fixed in the counterbore 322 and/or bore 320.

When the knee arthroplasty system 500 is assembled, the tibial prosthesis 304 articulates against the femoral prosthesis 502 to provide a range of motion between the tibial and femoral prostheses. The second articular portion 390 of the tibial articular insert 310 articulates with the shaft 328 of the adapter 508 to modify the nominal range of motion that would be possible if the second articular portion 390 and/or post 316 were absent. The knee arthroplasty system 500 has enhanced stability in use compared to a design that lacks the hinge constraint features of the second articular portion 390 and the post 316. More specifically, with reference to FIGS. 55-58, when the knee arthroplasty system 500 is in extension, the tibial prosthesis 304 has little to no translation relative to the femoral prosthesis 502 along directions that are perpendicular to the axis 503. Specifically, FIG. 56 shows that the tibial prosthesis 304 has little to no anterior-posterior translation and FIG. 58 shows that the tibial prosthesis has little to no medial-lateral translation. With reference to FIGS. 35 and 36 for knee arthroplasty system 300, when the knee arthroplasty system 500 is in flexion, the tibial prosthesis 304 has little to no translation along a direction that is parallel to the axis 503. Specifically, FIG. 36 shows that the tibial prosthesis 304 has little to no superior translation. The tibial prosthesis 304 also has little to no medial-lateral translation in flexion.

With reference to FIGS. 59-60, the adapter 508 is insertable into, fixable within, and removable from the receptacle 424 along an anterior-posterior direction that is perpendicular to the axis 503, from the anterior articular side 416 toward the posterior bone-facing side 414, while the femoral prosthesis 502 is fixed to a distal femur. The adapter 508 is interchangeable with other anterior adapters, such as adapter 408. Adapters can be exchanged before or after the femoral component 406 is fixed to the distal femur, even in a subsequent surgery.

A surgical method of implanting the knee arthroplasty system 500 may include some or all of the following steps in any order.

Preparing the distal femur may include making anterior, anterior chamfer, distal, posterior chamfer, and posterior resections to complement the bone-facing side 414 of the femoral component 406; drilling a hole to receive the socket 420, with or without a femoral intramedullary stem (not shown); and/or making a box cut to receive the pedestal 418 and/or adapter 508.

Fixing the femoral component 406 to the distal femur may include applying bone cement to the distal femur and/or the bone-facing side 414 of the femoral component 406, or press-fitting the femoral component 406 to the distal femur. Fasteners may be used to fix the femoral component to the distal femur.

Fixing the adapter 508 to the femoral component 406 may include extending or flexing the knee; sliding the adapter body 512 into the receptacle 424 from anterior to posterior; sliding the medial and lateral arms 566, 568 into the window 446; and fixing the adapter body to the femoral component. Optional fasteners may be used to fix the adapter to the femoral component. Preferably at this step, the adapter body 512 is coupled to at least the sleeve 314 and the pin 318.

Preparing the proximal tibia may include making a proximal tibial resection to complement the bone-facing side 192 of the tibial baseplate 112; and drilling a hole to receive the boss 196, with or without a tibial intramedullary stem (not shown).

Fixing the tibial baseplate 112 to the proximal tibia may include applying bone cement to the proximal tibia and/or the bone-facing side 192 of the tibial baseplate 112, or press-fitting the tibial baseplate 112 to the proximal tibia. Fasteners may be used to fix the tibial baseplate to the proximal tibia.

Coupling the tibial articular insert 310 to the tibial baseplate may include fixing the tibial articular insert to the tibial baseplate, or engaging mobile bearing features of the tibial articular insert and the tibial baseplate.

A surgical method of revising the knee arthroplasty system 500 may include some or all of the following steps in any order. Placing a previously-operated knee joint in extension or flexion; exposing the adapter 508; releasing the post 316 from fixation to the sleeve 314; removing the post 316 from the holes 202, 390, bore 320, and counterbore 322; releasing the adapter body 512 from fixation to the femoral component 406; removing the adapter body from the receptacle along a posterior-to-anterior direction; inserting a different adapter into the receptacle along an anterior-to-posterior direction; fixing the different adapter to the femoral component 406; and closing the incision. The tibial articular insert 310 may be disconnected from the tibial baseplate 112 to facilitate access to the adapter 508, and optionally reconnected after the different adapter has been fixed to the femoral component. The tibial articular insert 310 may be replaced with a different tibial articular insert during the same revision surgical procedure, for example to convert between CCK and hinged or fixed and mobile designs.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. An arthroplasty system for a joint between a first bone and a second bone, the system comprising:
   a first arthroplasty prosthesis with a receptacle, wherein the first arthroplasty prosthesis is configured to be fixed to the first bone and to articulate against a second arthroplasty prosthesis which is configured to be fixed to the second bone, so as to provide a range of motion between the first and second arthroplasty prostheses; and
   an adapter removably fixed in the receptacle, wherein the adapter comprises:
      a medial wall;
      a first protrusion coupled to the medial wall and extending medially therefrom;
      a lateral wall;
      a second protrusion coupled to the lateral wall and extending laterally therefrom; and
      a first constraint feature positioned between the medial wall and the lateral wall that is configured for constrained articulation against a complementary second constraint feature of the second arthroplasty prosthesis to modify the range of motion;
   wherein the first constraint feature comprises a cavity;
   wherein the second constraint feature comprises a protrusion received in the cavity so that when the joint is extended, the second arthroplasty prosthesis has limited translation along a direction that is generally perpendicular to a mechanical axis of the first bone, and so that when the joint is flexed, the second arthroplasty prosthesis has limited translation along a direction that is generally parallel to the mechanical axis of the first bone.

2. The system of claim 1, wherein the adapter is insertable into, fixable within, and removable from the receptacle when the first arthroplasty prosthesis is fixed to the first bone.

3. The system of claim 2, wherein the adapter goes into the receptacle along a direction that is generally parallel to a mechanical axis of the first bone when the first arthroplasty prosthesis is fixed to the first bone.

4. The system of claim 3, wherein the receptacle comprises an alcove extending into the first arthroplasty prosthesis along the direction, a first insertion stop feature, and a first removal stop feature, wherein the alcove comprises a non-circular cross-sectional shape perpendicular to the direction;

wherein the adapter comprises a non-circular exterior cross-sectional shape perpendicular to the direction, a second insertion stop feature, and a second removal stop feature, wherein the adapter exterior cross-sectional shape is complementary to the alcove cross-sectional shape;

wherein when the adapter is in the receptacle, the adapter exterior cross-sectional shape fits closely within the alcove cross-sectional shape, the first and second insertion stop features are engaged to prevent over-insertion of the adapter into the receptacle, and the first and second removal stop features are engaged to prevent unintentional removal of the adapter out of the receptacle, wherein the first and second removal stop features are disengageable.

5. The system of claim 2, wherein the adapter goes into the receptacle along a direction that is generally perpendicular to a mechanical axis of the first bone when the first arthroplasty prosthesis is fixed to the first bone.

6. The system of claim 5, wherein the receptacle comprises an alcove extending into the first arthroplasty prosthesis along the direction, a first insertion stop feature, and a first removal stop feature, wherein the alcove comprises a non-circular cross-sectional shape perpendicular to the direction;

wherein the adapter comprises a non-circular exterior cross-sectional shape perpendicular to the direction, a second insertion stop feature, and a second removal stop feature, wherein the adapter exterior cross-sectional shape is complementary to the alcove cross-sectional shape;

wherein when the adapter is in the receptacle, the adapter exterior cross-sectional shape fits closely within the alcove cross-sectional shape, the first and second insertion stop features are engaged to prevent over-insertion of the adapter into the receptacle, and the first and second removal stop features are engaged to prevent unintentional removal of the adapter out of the receptacle, wherein the first and second removal stop features are disengageable.

7. The system of claim 1, wherein the first constraint feature comprises a main body coupled to a sleeve by a hinge so that the sleeve rotates relative to the main body about a hinge axis, wherein the sleeve comprises a bore;

wherein the first constraint feature further comprises a shaft that is fixed in the bore;

wherein the second constraint feature comprises a hole that receives the shaft, so that the shaft rotates within the hole about a central longitudinal shaft axis and translates within the hole along the shaft axis.

8. An arthroplasty system for a joint between a first bone and a second bone, the system comprising:

a first arthroplasty prosthesis configured to be fixed to the first bone, wherein the first arthroplasty prosthesis comprises a receptacle;

an adapter removably fixed in the receptacle, wherein the adapter comprises a first constraint feature; and a second arthroplasty prosthesis comprising a bone-facing side configured to be fixed to the second bone and a superior side opposite the bone-facing side configured to couple with a mobile bearing feature of an articular insert, wherein the first and second arthroplasty prostheses articulate together to provide a range of motion between the first and second arthroplasty prostheses, wherein the second arthroplasty prosthesis comprises a second constraint feature that articulates against the first constraint feature to increase stability of the first arthroplasty prosthesis relative to the second arthroplasty prosthesis;

wherein the adapter is insertable into, fixable within, and removable from the receptacle when the first arthroplasty prosthesis is fixed to the first bone;

wherein the adapter goes into the receptacle along a direction that is generally parallel to a mechanical axis of the first bone when the first arthroplasty prosthesis is fixed to the first bone;

wherein the receptacle comprises an alcove extending into the first arthroplasty prosthesis along the direction, a first insertion stop feature, and a first removal stop feature, wherein the alcove comprises a non-circular cross-sectional shape perpendicular to the direction;

wherein the adapter comprises a non-circular exterior cross-sectional shape perpendicular to the direction, a second insertion stop feature, and a second removal stop feature, wherein the adapter exterior cross-sectional shape is complementary to the alcove cross-sectional shape;

wherein when the adapter is in the receptacle, the adapter exterior cross-sectional shape fits closely within the alcove cross-sectional shape, the first and second insertion stop features are engaged to prevent over-insertion of the adapter into the receptacle, and the first and second removal stop features are engaged to prevent unintentional removal of the adapter out of the receptacle, wherein the first and second removal stop features are disengageable.

9. The system of claim 8, wherein the adapter is insertable into, fixable within, and removable from the receptacle when the first arthroplasty prosthesis is fixed to the first bone; wherein the adapter goes into the receptacle along a direction that is generally perpendicular to a mechanical axis of the first bone when the first arthroplasty prosthesis is fixed to the first bone.

10. The system of claim 9, wherein the receptacle comprises an alcove extending into the first arthroplasty prosthesis along the direction, a first insertion stop feature, and a first removal stop feature, wherein the alcove comprises a non-circular cross-sectional shape perpendicular to the direction;

wherein the adapter comprises a non-circular exterior cross-sectional shape perpendicular to the direction, a second insertion stop feature, and a second removal stop feature, wherein the adapter exterior cross-sectional shape is complementary to the alcove cross-sectional shape;

wherein when the adapter is in the receptacle, the adapter exterior cross-sectional shape fits closely within the alcove cross-sectional shape, the first and second insertion stop features are engaged to prevent over-insertion of the adapter into the receptacle, and the first and second removal stop features are engaged to prevent unintentional removal of the adapter out of the receptacle, wherein the first and second removal stop features are disengageable.

11. The system of claim 8, wherein the first constraint feature comprises a cavity;

wherein the second constraint feature comprises a protrusion received in the cavity so that when the joint is extended, the second arthroplasty prosthesis has limited translation along a direction that is generally perpendicular to a mechanical axis of the first bone, and so that when the joint is flexed, the second arthroplasty prosthesis has limited translation along a direction that is generally parallel to the mechanical axis of the first bone.

12. The system of claim 8, wherein the first constraint feature comprises a main body coupled to a sleeve by a hinge so that the sleeve rotates relative to the main body about a hinge axis, wherein the sleeve comprises a bore;

wherein the first constraint feature further comprises a shaft that is fixed in the bore;

wherein the second constraint feature comprises a hole that receives the shaft, so that the shaft rotates within the hole about a central longitudinal shaft axis and translates within the hole along the shaft axis.

13. An arthroplasty system for a joint between a first bone and a second bone, the system comprising:

an adapter comprising:

a first constraint feature, wherein the adapter is removably fixable to a first arthroplasty prosthesis, wherein the first arthroplasty prosthesis is configured to be fixed to the first bone; and an anterior wall shaped to form at least a portion of an articular surface of the first arthroplasty prosthesis; and a second arthroplasty prosthesis comprising a second constraint feature, wherein the second arthroplasty prosthesis is configured to be fixed to the second bone and to articulate against the first arthroplasty prosthesis;

wherein the second constraint feature articulates against the first constraint feature to increase stability of the first arthroplasty prosthesis relative to the second arthroplasty prosthesis;

wherein the adapter is fixable to, and removable from, the first arthroplasty prosthesis when the first arthroplasty prosthesis is fixed to the first bone;

wherein the adapter is fixable to, and removable from, the first arthroplasty prosthesis along a direction that is generally perpendicular to a mechanical axis of the first bone when the first arthroplasty prosthesis is fixed to the first bone.

14. The system of claim 13, wherein the adapter is fixable to, and removable from, the first arthroplasty prosthesis along a direction that is generally parallel to a mechanical axis of the first bone when the first arthroplasty prosthesis is fixed to the first bone.

15. The system of claim 13, wherein the first constraint feature comprises a cavity;

wherein the second constraint feature comprises a protrusion received in the cavity so that when the joint is extended, the second arthroplasty prosthesis has limited translation along a direction that is generally perpendicular to a mechanical axis of the first bone, and so that when the joint is flexed, the second arthroplasty prosthesis has limited translation along a direction that is generally parallel to the mechanical axis of the first bone.

16. The system of claim 13, wherein the first constraint feature comprises a main body coupled to a sleeve by a hinge so that the sleeve rotates relative to the main body about a hinge axis, wherein the sleeve comprises a bore;

wherein the first constraint feature further comprises a shaft that is fixed in the bore;

wherein the second constraint feature comprises a hole that receives the shaft, so that the shaft rotates within the hole about a central longitudinal shaft axis and translates within the hole along the shaft axis.

17. An arthroplasty system for a joint between a first bone and a second bone, the system comprising:

a first arthroplasty prosthesis configured to be fixed to the first bone, wherein the first arthroplasty prosthesis comprises a receptacle;

an adapter removably fixed in the receptacle, wherein the adapter comprises a first constraint feature; and a second arthroplasty prosthesis comprising a bone-facing side configured to be fixed to the second bone and a superior side opposite the bone-facing side configured to couple with a mobile bearing feature of an articular insert, wherein the first and second arthroplasty prostheses articulate together to provide a range of motion between the first and second arthroplasty prostheses, wherein the second arthroplasty prosthesis comprises a second constraint feature that articulates against the first constraint feature to increase stability of the first arthroplasty prosthesis relative to the second arthroplasty prosthesis;

wherein the first constraint feature comprises a main body coupled to a sleeve by a hinge so that the sleeve rotates relative to the main body about a hinge axis, wherein the sleeve comprises a bore;

wherein the first constraint feature further comprises a shaft that is fixed in the bore;

wherein the second constraint feature comprises a hole that receives the shaft, so that the shaft rotates within the hole about a central longitudinal shaft axis and translates within the hole along the shaft axis.

18. The system of claim 17, wherein the first constraint feature comprises a cavity;

wherein the second constraint feature comprises a protrusion received in the cavity so that when the joint is extended, the second arthroplasty prosthesis has limited translation along a direction that is generally perpendicular to a mechanical axis of the first bone, and so that when the joint is flexed, the second arthroplasty prosthesis has limited translation along a direction that is generally parallel to the mechanical axis of the first bone.

* * * * *